US011207290B2

(12) United States Patent
Brener et al.

(10) Patent No.: US 11,207,290 B2
(45) Date of Patent: Dec. 28, 2021

(54) COMBINATIONS OF CANNABINOIDS AND N-ACYLETHANOLAMINES

(71) Applicant: SciSparc Ltd., Tel Aviv (IL)

(72) Inventors: Ephraim Brener, Rishon LeZion (IL); Elran Haber, Kiryat-Ono (IL); Ascher Shmulewitz, Tel Aviv (IL)

(73) Assignee: SciSparc Ltd., Tel Aviv (IL)

( * ) Notice: Subject to any disclaimer, the term of this patent is extended or adjusted under 35 U.S.C. 154(b) by 0 days.

(21) Appl. No.: 16/557,379

(22) Filed: Aug. 30, 2019

(65) Prior Publication Data

US 2020/0022946 A1 Jan. 23, 2020

Related U.S. Application Data

(62) Division of application No. 15/570,118, filed as application No. PCT/IL2016/050414 on Apr. 19, 2016.

(60) Provisional application No. 62/154,144, filed on Apr. 29, 2015.

(51) Int. Cl.
| | |
|---|---|
| *A61K 31/352* | (2006.01) |
| *A61K 31/164* | (2006.01) |
| *A61K 45/06* | (2006.01) |
| *A61P 25/04* | (2006.01) |
| *A61P 25/30* | (2006.01) |
| *A61P 25/14* | (2006.01) |
| *A61P 25/00* | (2006.01) |
| *A61P 29/00* | (2006.01) |
| *A61K 36/185* | (2006.01) |

(52) U.S. Cl.
CPC .......... *A61K 31/352* (2013.01); *A61K 31/164* (2013.01); *A61K 36/185* (2013.01); *A61K 45/06* (2013.01); *A61P 25/00* (2018.01); *A61P 25/14* (2018.01); *A61P 25/30* (2018.01); *A61P 29/00* (2018.01)

(58) Field of Classification Search
CPC ...... A61K 31/352; A61K 31/164; A61P 25/02
See application file for complete search history.

(56) References Cited

U.S. PATENT DOCUMENTS

| 6,949,582 B1 | 9/2005 | Wallace |
| 2002/0173550 A1 | 11/2002 | Calignano |

FOREIGN PATENT DOCUMENTS

| WO | WO2007/006319 A2 | 1/2007 | |
| WO | WO-2007052013 A1 * | 5/2007 | ........... A61K 31/047 |

OTHER PUBLICATIONS

Hesselink et al (Journal of Pain Research, 2012; 5:437-442) (Year: 2012).*
Hesselink (The Open Pain Journal, 2012, 5, 12-23) (Year: 2012).*
Ahn, K. et al. "Fatty acid amide hydrolase as a potential therapeutic target for the treatment of pain and CNS disorders", NIH Public Access, Expert Opin.Drug Discov. Jul. 2009; 4(7): 763-784.
Ho, W. SV et al., "Entourage effects of N-palmitoylethanolamide and N-oleoylethanolamide on vasorelaxation to anandamide occur though TRPV1 receptors", British Journal of Pharmacology (2008) 155, 837-846.
Watanabe K. et al., "Cytochrome P450 enzymes involved in the metabolism of tetrahydrocannabinols and cannabinol by human hepatic microsomes", Elsevier ScienceDirect, Life Sciences 80 (2007) 1415-1419.
Written Opinion dated Aug. 14, 2016 in corresponding Application No. PCT/IL2016/050414.
PCT International Search Report dated Aug. 14, 2016 in corresponding Application No. PCT/IL2016/050414.
Ben-Shabat et al., An Entourage Effect: Inactive Endogenous Fatty Acid Glycerol Esters Enhance 2-Arachidonoyl-Glycerol Cannabinoid Activity, Elsevier Science B.V., European Journal of Pharmacology, 1998.
D.M. Buxbaum,, Anagesic Activity of $\Delta^9$-Tetrahydrocannabinol in the Rat and Mouse, Psychopharmacologia (Berl.) 1972.
El-Alry et al., Antidepressent-like Effect of A9-Tetrahydrocannabinol and Other Cannabinoids Isolated from *Cannabis sativa* L, Pharmacol Biochem Behav. Jun. 2010.
Metrik, et al., Acute Effects of Marijuana Smoking on Negative and Positive Affect, J Cogn. Psychother, Feb. 2011.
Müller et al., $\Delta^9$-Tetrahydrocannabinol (THC) is Effective iin the Treatment of Tics in Tourette Syndrome: a 6 Week Randomized Trial, J Clin Psychiatry, 2003.
K.R. Müller-Vahl et al., Treatment of Tourette's Syndrome with $\Delta^9$-Tetrahydrocannabinol (THC): A Randomized Crossover Trial, Pharmacopsychiatry 2002.
Kirsten R. Müller-Vahl, Treatment of Tourette Syndrome with Cannabinoids, ISSN 2013.
Takagi et al., A Modification of Haffner's Method for Testing Analgesics, J.P.J. Pharmacol 1966.
H. Wagner, et al., Synergy Research: Approaching a new Generation of Phytopharmaceuticals, Elsevier GmbH, 2009.
M. Coppola et al., Palmitoylethandolamide: From Endogenous Cannabimimetic Substance to Innovative Medicine for the Treatment of Cannabis Dependence, Elsevier 2013.
Kirsten R. Müller-Vahl, et al., Treatment of Tourette Syndrome with Delta-9-Tetrahydrocannabinol ($\Delta^9$-THC) : No Influence on Neuropsychological Performance, Neuropsychopharmacology 2003.
THC and Opiates: "Entourage Effect" of Prismic's IP-Protected Palmitoylethanolamide Drives New Prescription Drug Safety, Prsmic Pharmaceuticals, Inc. Feb. 2015.
Extended European Search Report dated Nov. 26, 2018 for corresponding application No. PCT/IL2016/050414.
Weber et al., Tetrahydrocannabinol (Delta 9-THC) Treatment in Chronic Central Neuropathic Pain and Fibromyalgia Patients: Results of a Multicenter Survey, Anesthesiology Research and Practice, vol. 2009, Article ID 827290, 2009.

(Continued)

*Primary Examiner* — Marcos L Sznaidman
*Assistant Examiner* — Rayna Rodriguez
(74) *Attorney, Agent, or Firm* — Finnegan, Henderson, Farabow, Garrett & Dunner, L.L.P.

(57) ABSTRACT

The present invention provides pharmaceutical compositions comprising cannabinoids and N-acylethanolamines, and methods for their use in preventing and treating a variety of cannabinoid-treatable conditions.

17 Claims, 6 Drawing Sheets

(56) References Cited

OTHER PUBLICATIONS

Del Giorno et al., Palmitoylethanolamide in Fibromyalgia: Results from Prospective and Retrospective Observational Studies, Pain Therapy, 4:129-178, 2015.

Rahimi et al., Interaction between the protective effects of cannabidiol and palmitoylethanolamide in experimental model of multiple sclerosis in C57BL/6 mice; Neuroscience, Jan. 2015, pp. 279-297, vol. 290.

* cited by examiner

COMBINATIONS OF CANNABINOIDS AND N-ACYLETHANOLAMINES

RELATED APPLICATIONS

This is a divisional application of U.S. patent application Ser. No. 15/570,118, filed Oct. 27, 2017, which is a national stage application under 35 U.S.C. § 371 of International Application No. PCT/IL2016/050414, filed Apr. 19, 2016, which claims priority under 35 U.S.C. § 119 to U.S. Provisional Application No. 62/154,144, filed Apr. 29, 2015, each of which is expressly incorporated herein by reference in its entirety.

FIELD OF THE INVENTION

The present invention relates to compositions and methods for potentiating therapeutic effects and/or reducing side-effects of selected cannabinoids of the plant genus *Cannabis*. The present invention provides pharmaceutical compositions comprising cannabinoids and N-acylethanolamines, and methods for their use in a variety of indications amenable to treatment with cannabinoids.

BACKGROUND OF THE INVENTION

Cannabinoids are a class of diverse chemical compounds that act on cannabinoid receptors on cells that repress neurotransmitter release in the brain. Cannabinoid receptors are of a class of cell membrane receptors under the G protein-coupled receptor superfamily. As is typical of G protein-coupled receptors, the cannabinoid receptors contain seven transmembrane spanning domains. There are currently two known subtypes of cannabinoid receptors, termed CB1 and CB2, with mounting evidence of more. The CB1 receptor is expressed mainly in the brain (central nervous system), but also in the lungs, liver and kidneys. The CB2 receptor is expressed mainly in the immune system and in hematopoietic cells. The protein sequences of CB1 and CB2 receptors are about 44% similar.

Phyto-cannabinoids (those derived from the *Cannabis* plant) include but not limited to: tetrahydrocannabinol (THC), tetrahydrocannabinolic acid (THCA), cannabidiol (CBD), cannabinol (CBN), Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV) and Cannabigerol Monomethyl Ether (CBGM). The main way in which the cannabinoids are differentiated is based on their degree of psycho-activity. For example, CBG, CBC and CBD are not known to be psychologically active agents whereas THC, THCA, CBN and CBDL along with some other cannabinoids are known to have varying degrees of psycho-activity.

The most notable cannabinoid is the phyto-cannabinoid Δ9-tetrahydrocannabinol (THC), which is the primary psychoactive component of the *Cannabis* plant. THC has approximately equal affinity for the CB1 and CB2 receptors, and it possess activities as a psycho-active agent, analgesic, muscle relaxant, anti-spasmodic, bronchodilator, neuro-protective, anti-oxidant and anti-pruritic agent.

Dronabinol is the International Nonproprietary Name (INN) for a pure isomer of THC, (−)-trans-Δ9-tetrahydrocannabinol. Synthesized dronabinol is marketed as Marinol. Marinol has been approved by the U.S. Food and Drug Administration (FDA) in the treatment of anorexia in AIDS patients, as well as for refractory nausea and vomiting of patients undergoing chemotherapy. An analog of dronabinol, nabilone, a Schedule H drug with therapeutic use as an antiemetic and as an adjunct analgesic for neuropathic pain, is available commercially in Canada under the trade name Cesamet. Cesamet has also received FDA approval and began marketing in the U.S. in 2006.

Sativex is the first natural *Cannabis* plant derivative to gain full market approval. Sativex is a mouth spray for multiple sclerosis (MS)-derived neuropathic pain, spasticity, overactive bladder, and other symptoms. Each spray delivers a near 1:1 ratio of Cannabidiol (CBD) to THC, with a fixed dose of 2.7 mg THC and 2.5 mg CBD.

Tourette syndrome (also called Tourette's syndrome, Tourette's disorder, Gilles de la Tourette syndrome, GTS or, more commonly, simply Tourette's or TS) is an inherited neuropsychiatric disorder with onset in childhood, characterized by multiple physical (motor) tics and at least one vocal (phonic) tic. Tourette's is defined as part of a spectrum of tic disorders, which includes provisional, transient and persistent (chronic) tics.

In Tourette syndrome, several anecdotal reports provided evidence that marijuana might be effective not only in the suppression of tics, but also in the treatment of associated behavioral problems (Muller-Vahl K R, Behavioural Neurology, 2013, 27, 119-124). There are currently only two controlled trials available investigating the effect of THC in the treatment of TS, and in both studies tic reduction could be observed after treatment with THC compared to placebo. In the first study, adult TS patients were treated with a single dose of placebo or with 5, 7.5 or 10 mg THC (Muller-Vahl K R et al., Pharmacopsychiatry, 2002; 35(2): 57-61). Using the self-rating scale Tourette Syndrome Symptom List (TSSL) a significant global tic improvement was found after THC compared with placebo (p=0.015). However, the data became more robust when including only those patients who had received 7.5 or 10.0 mg THC, suggesting that higher dosages are more effective. In the second study, adult TS patients were treated with placebo or with 2.5 mg THC per day. The dosage was increased by 2.5 mg every four days to the target dosage of 10 mg. If a patient was unable to tolerate the maximum dose, the medication was reduced by up to 5.0 mg/day until a tolerated dose was achieved (Muller-Vahl K R et al, J. Clin. Psychiatry, 2003; 64(4): 459-65). The study consisted of 6 visits (visit 1=baseline, visits 2-4 during treatment, visits 5 and 6 after withdrawal). Using the Global Clinical Impression Scale (GCIS), at visits 3 and 4, respectively, a significant difference (p<0.05) was found between the THC and placebo groups.

Further limitations and disadvantages of conventional and traditional approaches will become apparent to one of skill in the art, though comparison of such systems with some aspects of the present invention as set forth in the remainder of the present application with reference to the drawings.

N-acylethanolamines (NAEs) are lipid-derived signaling molecules. They are formed when one of several types of acyl group is linked to the nitrogen atom of ethanolamine. Examples of N-acylethanolamines include anandamide (the amide of arachidonic acid (20:4 ω-6) and ethanolamine), N-Palmitoylethanolamine (the amide of pahnitic acid (16:0) and ethanolamine), N-Oleoylethanolamine (the amide of oleic acid (18:1) and ethanolamine), N-Stearoylethanolamine (the amide of stearic acid (18:0) and ethanolamine) and N-Docosahexaenoylethanolamine (the amide of docosahexaenoic acid (22:6) and ethanolamine).

Pahnitoylethanolamide (PEA, also known as N-(2-hydroxyethyl)hexadecanamide; Hydroxyethylpalmitamide; palmidrol; N-palmitoylethanolamine; and palmitylethanolamide) is an endogenous fatty acid amide, belonging to the class of nuclear factor agonists. PEA has been demonstrated to bind to a receptor in the cell nucleus (a nuclear receptor) and exerts a variety of biological functions related to chronic pain and inflammation. Studies have shown that PEA interacts with distinct non-CB1/CB2 receptors, suggesting that PEA utilizes a unique "parallel" endocannabinoid signaling system. This concept was further supported by growing evidences that PEA production and inactivation can occur independently of AEA and 2-AG production and inactivation. Much of the biological effects of PEA on cells can be attributed to its affinity to PPAR (particularly PPAR-α and PPAR-γ). PEA was shown to have an affinity to cannabinoid-like G-coupled receptors GPR55 and GPR119 as well as the transient receptor potential vanilloid type 1 receptor (TRPV1). PEA has been shown to have anti-inflammatory, anti-nociceptive, neuro-protective, and anti-convulsant properties.

First described by S. Ben-Shabat et al. (Eur. J. Pharmacol., 1998, Vol. 353(1), pages 23-31), the concept of the "entourage effect" is that plant cannabinoids act together, or possess synergy, and affect the body in a mechanism similar to the body's own endocannabinoid system. This theory serves as the foundation for a somewhat controversial idea within pharmacology, that in certain cases whole plant extractions serve as better therapeutic agents than individual cannabinoid extractions. The "entourage effect" theory has been expanded in recent times by Wagner and Ulrich-Merzenich (Phytomedicine, 2009, Vol. 16(2-3), pages 97-110), who define the four basic mechanisms of whole plant extract synergy as follows: (a) ability to affect multiple targets within the body, (b) ability to improve the absorption of active ingredients, (c) ability to overcome bacterial defense mechanisms, and (d) ability to minimize adverse side-effects.

There remains a need in the field of cannabinoid therapy for pharmaceutical combinations of cannabinoids and other agents capable of increasing the potency, decreasing the therapeutic dosages, reducing the side-effects and/or prolonging the therapeutic window of cannabinoids, particularly THC, in humans.

SUMMARY OF THE INVENTION

The present invention provides pharmaceutical compositions comprising beneficial combinations of cannabinoids and N-acylethanolamines. These combinations are defined, in part, by specific molar ratios between the respective active agents and/or by their dosages, and may be employed in a variety of methods. Particularly, the present invention provides methods for preventing and/or treating a variety of conditions responsive to cannabinoid treatment such as movement disorders, for example Tourette's syndrome and related symptoms. In addition, the present invention provides methods for preventing and/or treating conditions associated with cannabinoid uptake, such as body-weight gain, confusion, disorientation and anxiety. Furthermore, the present invention provides methods for increasing the therapeutic effect associated with cannabinoid uptake, such as prevention or amelioration of pain.

The provision of such combinations provides great benefits over other compositions and methods utilizing cannabinoids alone. For example, the methods provided herein potentiate the therapeutic effect of prescribed cannabinoids, which may be clinically translated to a more beneficial therapeutic result or to the use of lower dosages of cannabinoids to obtain a predetermined therapeutic result. The methods provided herein further advantageously eliminate or substantially minimize adverse side-effects commonly associated with cannabinoid uptake in Cannabis-prescribed patients. In other words, according to the principles of the present invention, the therapeutic window (or pharmaceutical window) of the cannabinoid, i.e. the range of cannabinoid dosages which can treat disease effectively without having toxic effects, is expended by the combinations provided herein.

The present invention is based, in part, on the surprising findings that combinations of cannabinoids and N-acylethanolarnines were able to prevent or ameliorate a variety of side-effects associated with cannabinoid consumption in an in-vivo model, and that these combinations were further able to increase the effect of cannabinoids as analgesic agents. Without being bound to any theory or mechanism, it is hypothesized that co-administration of cannabinoids and N-acylethanolamines increases the potency of cannabinoids while decreasing their related side-effects, a phenomenon previously labeled "entourage effect".

The present invention provides, in one aspect, a pharmaceutical composition comprising a therapeutically-effective amount of a mixture of at least one cannabinoid or a salt thereof and at least one N-acylethanolamine or a salt thereof, wherein the molar ratio between the cannabinoid and the N-acylethanolamine is between about 1:0.2 to about 1:2000.

In certain embodiments, the molar ratio between the cannabinoid and the N-acylethanolamine is between about 1:0.2 to about 1:5. In certain embodiments, the molar ratio between the cannabinoid and the N-acylethanolamine is between about 1:0.5 to about 1:2. In certain embodiments, the molar ratio between the cannahinoid and the N-acylethanolamine is between about 1:15 to about 1:1800. In certain embodiments, the molar ratio between the cannabinoid and the N-acylethanolamine is between about 1:25 to about 1:450. In certain embodiments, the molar ratio between the cannabinoid and the N-acylethanolamine is between about 1:50 to about 1:100. In certain embodiments, the molar ratio between the cannabinoid and the N-acylethanolamine is about 1:50. In certain embodiments, the molar ratio between the cannabinoid and the N-acylethanolamine is about 1:100. Each possibility represents a separate embodiment of the present invention.

In certain embodiments, the pharmaceutical composition comprises about 0.5-10 mg cannahinoid or a salt thereof. In certain embodiments, the pharmaceutical composition comprises about 1 mg, about 2.5 mg, about 5 mg, or about 10 mg cannabinoid or a salt thereof. Each possibility represents a separate embodiment of the present invention.

In certain embodiments, the at least one cannabinoid is selected from tetrahydrocannabinol (THC), tetrahydrocannabinolic acid (THCA), cannabidiol (CBD), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof and any combination thereof. Each possibility represents a separate embodiment of the present invention. In certain embodiments, the at least one cannabinoid is THC or a salt thereof. In certain embodiments, the cannabinoid consists of THC or a salt thereof. In certain embodiments, cannabinoid consists of THC.

In certain embodiments, the pharmaceutical composition comprises about 200-1800 mg N-acylethanolamine or a salt thereof. In certain embodiments, the pharmaceutical composition comprises about 250 mg, about 500 mg, about 750 mg, about 1000 mg or about 1500 mg N-acylethanolamine or a salt thereof. Each possibility represents a separate embodiment of the present invention.

In certain embodiments, the N-acylethanolamine is selected from the group consisting of N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), salts thereof and any combination thereof. Each possibility represents a separate embodiment of the present invention. In certain embodiments, the N-acylethanolamine is PEA or a salt thereof. In certain embodiments, the N-acylethanolamine consists of PEA or a salt thereof. In certain embodiments, the N-acylethanolamine consists of PEA.

In certain embodiments, the mixture comprises THC or a salt thereof and PEA or a salt thereof. In certain embodiments, the mixture consists of THC or a salt thereof and PEA or a salt thereof. In certain embodiments, the mixture comprises THC and PEA. In certain embodiments, the mixture consists of THC and PEA. In certain embodiments, the mixture comprises about 0.5-10 mg THC or a salt thereof and about 200-1800 mg PEA or a salt thereof. In certain embodiments, the mixture consists of THC and PEA. In certain embodiments, the mixture comprises about 2.5-10 mg THC or a salt thereof and about 250-1000 mg PEA or a salt thereof. In certain embodiments, the mixture comprises about 2.5 mg, about 5 mg, about 7.5 mg or about 10 mg THC or a salt thereof and about 250 mg, about 500 mg, about 750 mg or about 1000 mg PEA or a salt thereof. Each possibility represents a separate embodiment of the present invention.

In certain embodiments, the pharmaceutical composition is formulated for systemic administration. In certain embodiments, the pharmaceutical composition is formulated for oral, oral mucosal, nasal, sublingual, inhalational, topical, rectal, vaginal, parenteral, intravenous, intramuscular, or subcutaneous administration. In certain embodiments, the pharmaceutical composition is formulated for oral, oral mucosal, nasal, or sublingual administration. Each possibility represents a separate embodiment of the present invention. In certain embodiments, the pharmaceutical composition is formulated for oral administration. In certain embodiments, the pharmaceutical composition is fointulated for oral mucosal administration. In certain embodiments, the pharmaceutical composition is formulated for nasal administration. In certain embodiments, the pharmaceutical composition is formulated for sublingual administration.

The present invention further provides, in another aspect, a dosage unit comprising or consisting of the pharmaceutical composition described above.

In certain embodiments, the dosage unit comprises the pharmaceutical composition described above. In certain embodiments, the dosage unit consisting of the pharmaceutical composition described above. In certain embodiments, the dosage unit is formulated as a gel, a powder or a spray. In certain embodiments, the dosage unit is formulated as a gel. In certain embodiments, the dosage unit is formulated as a powder. In certain embodiments, the dosage unit is formulated as a spray.

The present invention further provides, in another aspect, a pharmaceutical composition or a dosage unit as described above for use in a method for preventing or treating a condition amenable to prevention or treatment by at least one cannabinoid.

The present invention further provides, in another aspect, a pharmaceutical composition or a dosage unit as described above for use in a method for preventing or treating at least one symptom of Tourette syndrome.

In certain embodiments, the Tourette syndrome is classified as mild Tourette syndrome. In certain embodiments, the Tourette syndrome is classified as moderate Tourette syndrome. In certain embodiments, the Tourette syndrome is classified as severe Tourette syndrome. In certain embodiments, the Tourette syndrome is classified as a moderate to severe Tourette syndrome. In certain embodiments, the symptom is tics. In certain embodiments, the tics are motor tics. In certain embodiments, the tics are phonic tics. In certain embodiments, the tics are verbal tics. In certain embodiments, the tics are vocal tics. In certain embodiments, the tics are simple motor tics. In certain embodiments, the tics are complex motor tics. In certain embodiments, the tics are simple phonic tics. In certain embodiments, the tics are complex phonic tics.

The present invention further provides, in another aspect, a pharmaceutical composition or a dosage unit as described above for use in a method for preventing or treating pain.

In certain embodiments, the pain is an acute pain. In certain embodiments, the pain is chronic pain. In certain embodiments, the pain is neuropathic pain.

The present invention further provides, in another aspect, a pharmaceutical composition or a dosage unit as described above for use in a method for preventing or treating emesis.

The present invention further provides, in another aspect, a pharmaceutical composition or a dosage unit as described above for use in a method for preventing or treating at least one side-effect associated with cannabinoid consumption.

In certain embodiments, the side-effect is increased appetite. In certain embodiments, the side-effect is body-weight gain. In certain embodiments, the side-effect is increased appetite and body-weight gain. In certain embodiments, the side-effect is confusion. In certain embodiments, the side-effect is disorientation. In certain embodiments, the side-effect is confusion and disorientation. In certain embodiments, the side-effect is anxiety.

In certain embodiments, the condition is amenable to prevention or treatment by THC or a salt thereof. In certain embodiments, the side-effect is associated with THC consumption.

In certain embodiments, the N-acylethanolamine increases the therapeutic potency of the cannabinoid compared to the same pharmaceutical composition without the N-acylethanolamine. In certain embodiments, the N-acylethanolamine decreases the required therapeutic dosage of the cannabinoid compared to the same pharmaceutical composition without the N-acylethanolamine. In certain embodiments, the N-acylethanolamine reduces at least one of the side-effects of the cannabinoid compared to the same pharmaceutical composition without the N-acylethanolamine. In certain embodiments, the N-acylethanolamine expends the therapeutic window of the cannabinoid compared to the same pharmaceutical composition without the N-acylethanolamine. In certain embodiments, the PEA or salt thereof increases the therapeutic potency of the THC or salt thereof compared to the same pharmaceutical composition without the PEA or salt thereof. In certain embodiments, the PEA or salt thereof decreases the required therapeutic dosage of the THC or salt thereof compared to the same pharmaceutical composition without the PEA or salt thereof. In certain embodiments, the PEA or salt thereof reduces at least one of the side-effects of the THC or salt thereof compared to the same pharmaceutical composition without the PEA or salt thereof. In certain embodiments, the PEA or salt thereof expends the therapeutic window of the THC or salt thereof compared to the same pharmaceutical composition without the PEA or salt thereof.

The present invention further provides, in another aspect, a method for preventing or treating a condition amenable to prevention or treatment by at least one cannabinoid in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating the condition.

The present invention further provides, in another aspect, a method for preventing or treating at least one symptom of Tourette syndrome in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating the at least one symptom of Tourette syndrome.

The present invention further provides, in another aspect, a method for preventing or treating pain in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating pain.

The present invention further provides, in another aspect, a method for preventing or treating emesis in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating emesis.

The present invention further provides, in another aspect, a method for preventing or treating at least one side-effect associated with cannabinoid consumption in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating the at least one side-effect.

In certain embodiments of the methods described above, the cannabinoid and the N-acylethanolamine are comprised in the same pharmaceutical composition. In certain embodiments of the methods described above, the cannabinoid and the N-acylethanolamine are comprised in different pharmaceutical compositions.

In certain embodiments of the methods described above, the administration of the cannabinoid and the N-acylethanolamine is repeated three times a day. In certain embodiments of the methods described above, the administration of the cannabinoid and the N-acylethanolamine is repeated twice a day. In certain embodiments of the methods described above, the administration of the cannabinoid and the N-acylethanolamine is repeated once a day. In certain embodiments of the methods described above, the administration of the cannabinoid and the N-acylethanolamine is repeated once every two days. In certain embodiments of the methods described above, the administration of the cannabinoid and the N-acylethanolamine is repeated once every three days.

In certain embodiments of the methods described above, the administration of the cannabinoid and the N-acylethanolamine is repeated until achieving a beneficial change in the condition of the subject according to the Yale Global Tic Severity Scale (YGTSS) compared to his condition prior to treatment. In certain embodiments of the methods described above, the administration of the cannabinoid and the N-acylethanolamine is repeated until achieving a beneficial change in the condition of the subject according to at least one scale selected from the group consisting of (i) the Clinician Global Impression scale (CGIS), (ii) the Gilles de la Tourette Syndrome-Quality Of Life scale (GTS-QOL) (iii) the Tourette Syndrome Symptom List (TSSL) (iv) the Yale-Brown Obsessive Compulsive Scale (Y-BOCS) (v) the ADHD Rating Scale-IV (ADHD-RS) and (vi) the Hamilton Anxiety Rating Scale (HAM-A), compared to his condition prior to treatment. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
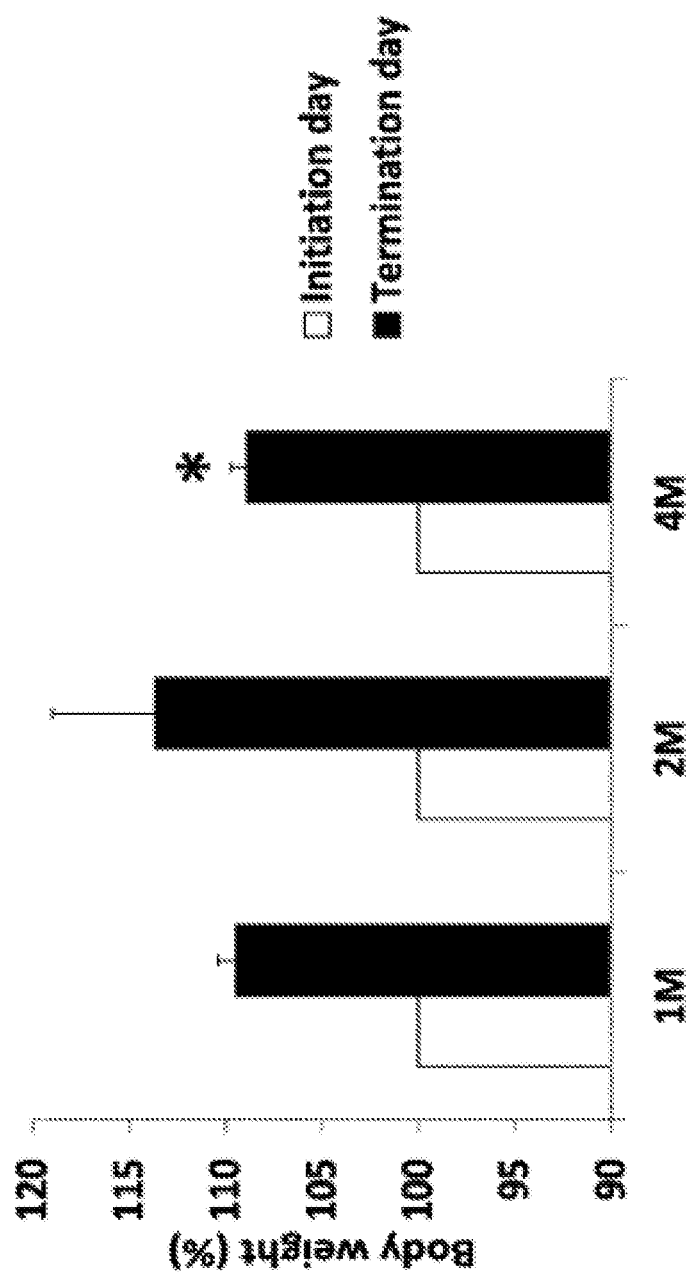
FIGS. 1A and 1B are bar graphs illustrating different group averages of body weight gain during the study.

*Cannabis* has been used for medical purposes in many cultures for hundreds of years, in particular, for the treatment of pain, spasms, asthma, insomnia, depression and loss of appetite. In the 1960s, the exact chemical structure of delta-9-tetrahydrocannabinol (THC), the main psychoactive ingredient of *Cannabis* sativa, has been be determined. Research on the medical use of cannabinoids was further stimulated when it became clear that cannabinoids act through specific receptors: CB1 receptors predominantly located in the central nervous system and CB2 receptors that are expressed primarily by immune tissues. Today, in many countries the cannabinoid THC and the *Cannabis* extract nabiximols containing THC and CBD are approved for clinical use for the treatment of nausea and vomiting associated with cancer chemotherapy, anorexia in HIV/AIDS, and spasticity in multiple sclerosis. There is substantial evidence that cannabinoids are also effective in the treatment of other conditions such as neuropathic pain, spasms and movement disorders (Muller-Vahl KR, Behavioural Neurology, 2013, 27, 119-124). However, it has also been found in controlled clinical trials that while higher dosages of THC (7.5-10 mg/day) are more effective than lower dosages (Muller-Vahl K R et al., Pharmacopsychiatry, 2002; 35(2): 57-61), some of the patients were unable to tolerate the maximum dose, and THC uptake was reduced by up to 5.0 mg/day until a tolerated dose was achieved (Muller-Vahl K R et al, J. Clin. Psychiatry, 2003; 64(4): 459-65).

The pharmaceutical combinations provided by the present invention, in which cannabinoids are combined with N-acylethanolamines, eliminate this inherent, adverse dichotomy between therapeutic efficacy and tolerability by potentiating the therapeutic effect of prescribed cannabinoids, which is clinically translated to a more beneficial therapeutic result or to the use of lower dosages of cannabinoids to obtain a predetermined therapeutic result. The pharmaceutical combinations provided by the present invention further advantageously eliminate or substantially minimize adverse side-effects commonly associated with cannabinoid uptake in *Cannabis*-prescribed patients. According to the principles of the present invention, the therapeutic window of the cannabinoids is expended by the pharmaceutical combinations provided herein such that (a) standard THC dosages, e.g. in the range of 5-10 mg THC daily are better tolerated due to reduced side-effects, and (b) standard THC dosages can be markedly reduced without compromising their therapeutic efficacy or the patient's health due to the increased efficacy of THC.

The present invention discloses that N-acylethanolamine compounds exhibit a cannabinoid-sparing effect. The term "cannabinoid-sparing" as used herein refers to the enablement of the use of low dosages of cannabinoids in instances wherein a mid- or high-dosages of cannabinoids are typically required. The cannabinoid and N-acylethanolamine compounds according to the present invention include pharmaceutically acceptable forms thereof, including isomers such as diastereomers and enantiomers, salts, solvates, and polymorphs, as well as racemic mixtures.

The present invention provides, in one aspect, a pharmaceutical composition comprising a therapeutically-effective amount of a mixture of at least one cannabinoid or a salt thereof and at least one N-acylethanolamine or a salt thereof.

The present invention provides, in another aspect, a pharmaceutical composition comprising a therapeutically-effective amount of a mixture of at least one cannabinoid or a salt thereof and at least one N-acylethanolamine or a salt thereof, wherein the molar ratio between the cannabinoid and the N-acylethanolamine is between about 1:0.2 to about 1:2000.

As used herein, a "pharmaceutical composition" refers to a preparation of the active agents described herein with other chemical components such as physiologically suitable carriers and excipients. The purpose of a pharmaceutical composition is to facilitate administration of a compound to an organism. As used herein, the phrase "pharmaceutically acceptable carrier" refers to a carrier, an excipient or a diluent that does not cause significant irritation to an organism and does not abrogate the biological activity and properties of the administered compound. An adjuvant is included under these phrases.

The term "excipient" as used herein refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, oils such as vegetable oils or fish oils, and polyethylene glycols.

The term "carrier" as used herein refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The phrase "pharmaceutically acceptable" as used herein refers to molecular entities and compositions that are physiologically tolerable and do not typically produce an allergic or similar toxicity when administered to an individual. Preferably, and particularly where a formulation is used in humans, the term "pharmaceutically acceptable" may mean approved by a regulatory agency (for example, the U.S. Food and Drug Agency) or listed in a generally recognized pharmacopeia for use in animals (e.g., the U.S. Pharmacopeia).

The term "cannabinoid" as used herein generally refers to a class of diverse chemical compounds that act on cannabinoid receptors on cells that repress neurotransmitter release in the brain. Ligands for these receptor proteins include the endocannabinoids (produced naturally in the body by humans and animals), the phytocannabinoids (found in *Cannabis* and some other plants), and synthetic cannabinoids (manufactured artificially). There are at least 85 different cannabinoids isolated from *Cannabis*, exhibiting varied effects (El-Alfy et al., Pharmacology Biochemistry and Behavior, 2010, Vol. 95(4), pages 434-442).

The term "N-acylethanolamine" as used herein generally refers to a type of fatty acid amide, lipid-derived signaling molecules, formed when one of several types of acyl group is linked to the nitrogen atom of ethanolamine. These amides conceptually can be formed from a fatty acid and ethanolamine with the release of a molecule of water, but the known biological synthesis uses a specific phospholipase D to cleave the phospholipid unit from N-acylphosphatidylethanolamines. The suffixes -amine and -amide in these names each refer to the single nitrogen atom of ethanolamine that links the compound together: it is termed "amine" in ethanolamine because it is considered as a free terminal nitrogen in that subunit, while it is termed "amide" when it is considered in association with the adjacent carbonyl group of the acyl subunit. Names for these compounds may be encountered with either "amide" or "amine" in the present application. The term "ethanolamine" is used in the generic sense and is meant to include mono-ethanolamine, di-ethanolamine, tri-ethanolamine, and mixtures thereof.

The term "derivative" as used herein means a compound whose core structure is the same as, or closely resembles that of an N-acylethanolamine compound, but which has a chemical or physical modification, such as different or additional side groups.

The term "salt" as used herein refers to any form of an active ingredient in which the active ingredient assumes an ionic form and is coupled to a counter ion (a cation or anion)

or is in solution. This also includes complexes of the active ingredient with other molecules and ions, in particular complexes which are complexed by ion interaction.

In certain embodiments, the molar ratio between the cannabinoid and the N-acylethanolamine is between about 1:0.2 to about 1:5. In certain embodiments, the molar ratio between the cannabinoid and the N-acylethanolamine is between about 1:0.22 to about 1:4.5, about 1:0.25 to about 1:4, between about 1:0.28 to about 1:3.5, between about 1:0.33 to about 1:3, between about 1:0.4 to about 1:2.5, between about 1:0.5 to about 1:2 or about 1:1. Each possibility represents a separate embodiment of the present invention.

In certain embodiments, the molar ratio between the cannabinoid and the N-acylethanolamine is between about 1:15 to about 1:1800. In certain embodiments, the molar ratio between the cannabinoid and the N-acylethanolamine is between about 1:16 to about 1:1700, about 1:17 to about 1:1600, about 1:18 to about 1:1500, about 1:19 to about 1:1400, about 1:20 to about 1:1300, about 1:21 to about 1:1200, about 1:22 to about 1:1100, about 1:23 to about 1:1000, about 1:24 to about 1:900, about 1:15 to about 1:800, about 1:16 to about 1:700, about 1:17 to about 1:600, about 1:18 to about 1:500, about 1:19 to about 1:490, about 1:20 to about 1:480, about 1:21 to about 1:470, or about 1:22 to about 1:460. Each possibility represents a separate embodiment of the present invention. In certain embodiments, the molar ratio between the cannabinoid and the N-acylethanolamine is between about 1:25 to about 1:450. In certain embodiments, the molar ratio between the cannabinoid and the N-acylethanolamine is between about 1:10 to about 1:500, about 1:15 to about 1:450, about 1:20 to about 1:400, about 1:25 to about 1:350, about 1:30 to about 1:300, about 1:35 to about 1:250, about 1:40 to about 1:200, or about 1:45 to about 1:150. Each possibility represents a separate embodiment of the present invention. In certain embodiments, the molar ratio between the cannabinoid and the N-acylethanolamine is between about 1:50 to about 1:100. In certain embodiments, the molar ratio between the cannabinoid and the N-acylethanolamine is about 1:10. In certain embodiments, the molar ratio between the cannabinoid and the N-acylethanolamine is about 1:20. In certain embodiments, the molar ratio between the cannabinoid and the N-acylethanolamine is about 1:30. In certain embodiments, the molar ratio between the cannabinoid and the N-acylethanolamine is about 1:40. In certain embodiments, the molar ratio between the cannabinoid and the N-acylethanolamine is about 1:50. In certain embodiments, the molar ratio between the cannabinoid and the N-acylethanolamine is about 1:60. In certain embodiments, the molar ratio between the cannabinoid and the N-acylethanolamine is about 1:70. In certain embodiments, the molar ratio between the cannabinoid and the N-acylethanolamine is about 1:80. In certain embodiments, the molar ratio between the cannabinoid and the N-acylethanolamine is about 1:90. In certain embodiments, the molar ratio between the cannabinoid and the N-acylethanolamine is about 1:100. In certain embodiments, the molar ratio between the cannabinoid and the N-acylethanolamine is about 1:110. In certain embodiments, the molar ratio between the cannabinoid and the N-acylethanolamine is about 1:120. In certain embodiments, the molar ratio between the cannabinoid and the N-acylethanolamine is about 1:130. In certain embodiments, the molar ratio between the cannabinoid and the N-acylethanolamine is about 1:140. In certain embodiments, the molar ratio between the cannabinoid and the N-acylethanolamine is about 1:150. In certain embodiments, the molar ratio between the cannabinoid and the N-acylethanolamine is about 1:160. In certain embodiments, the molar ratio between the cannabinoid and the N-acylethanolamine is about 1:170. In certain embodiments, the molar ratio between the cannabinoid and the N-acylethanolamine is about 1:180. In certain embodiments, the molar ratio between the cannabinoid and the N-acylethanolamine is about 1:190. In certain embodiments, the molar ratio between the cannabinoid and the N-acylethanolamine is about 1:200. In certain embodiments, the molar ratio between the cannabinoid and the N-acylethanolamine is at least about 1:10, at least about 1:20, at least about 1:30, at least about 1:40, at least about 1:50, at least about 1:60, at least about 1:70, at least about 1:80, at least about 1:90, or at least about 1:100. Each possibility represents a separate embodiment of the present invention.

In certain embodiments, the pharmaceutical composition comprises about 0.5-10 mg cannabinoid or a salt thereof. In certain embodiments, the pharmaceutical composition comprises about 1-9.5 mg, about 1.5-9 mg, about 2-8.5 mg, about 2.5-8 mg, about 3-7.5 mg, about 3.5-7 mg, about 4-6.5 mg, about 4.5-6 mg or about 5-5.5 mg cannabinoid or a salt thereof. In certain embodiments, the pharmaceutical composition comprises about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg or about 10 mg cannabinoid or a salt thereof. Each possibility represents a separate embodiment of the present invention. In certain embodiments, the pharmaceutical composition comprises less than about 0.5 mg, less than about 1 mg, less than about 1.5 mg, less than about 2 mg, less than about 2.5 mg, less than about 3 mg, less than about 3.5 mg, less than about 4 mg, less than about 4.5 mg, less than about 5 mg, less than about 5.5 rng, less than about 6 mg, less than about 6.5 mg, less than about 7 mg, less than about 7.5 mg, less than about 8 mg, less than about 8.5 mg, less than about 9 mg, less than about 9.5 mg or about 10 mg cannabinoid or a salt thereof. Each possibility represents a separate embodiment of the present invention. In certain embodiments, the pharmaceutical composition comprises about 0.5 mg to about 1 mg, about 0.5 mg to about 1.5 mg, about 0.5 mg to about 2 mg, about 0.5 mg to about 2.5 mg, about 0.5 mg to about 3 mg, about 0.5 mg to about 3.5 mg, about 0.5 mg to about 4 mg, about 0.5 mg to about 4.5 mg, about 0.5 mg to about 5 mg, about 0.5 mg to about 5.5 mg, about 0.5 mg to about 6 mg, about 0.5 mg to about 6.5 mg, about 0.5 mg to about 7 mg, about 0.5 mg to about 7.5 mg, about 0.5 mg to about 8 mg, about 0.5 mg to about 8.5 mg, about 0.5 mg to about 9 mg or about 0.5 mg to about 9.5 mg cannabinoid or a salt thereof. Each possibility represents a separate embodiment of the present invention.

In certain embodiments, the at least one cannabinoid is selected from tetrahydrocannabinol (THC), tetrahydrocannabinolic acid (THCA), cannabidiol (CBD), cannabinol (CSN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof and any combination thereof. Each possibility represents a separate embodiment of the present invention. In certain embodiments, the at least one cannabinoid is THC or a salt thereof and CBD or a salt thereof. In certain embodiments, the at least one cannabinoid consists of THC or a salt thereof and CBD or a salt thereof. In certain embodiments, the molar ratio between the THC or salt thereof and the CBD or salt thereof is between about 2:1 to about 1:2. In certain embodiments, the molar ratio between the THC or salt thereof and the CBD or salt thereof is about 1:1. In certain embodiments, the at least one cannabinoid is THC or a salt thereof. In certain embodiments, the at least one cannabinoid consists of THC or a salt thereof. In certain embodiments, the at least one cannabinoid consists of THC.

In certain embodiments, the pharmaceutical composition comprises about 200-1800 mg N-acylethanolamine or a salt thereof. In certain embodiments, the pharmaceutical composition comprises about 250-1550 mg, about 300-1200 mg, about 350-950 mg, about 400-700 mg, about 450-600 mg or about 500-550 mg N-acylethanolamine or a salt thereof. Each possibility represents a separate embodiment of the present invention. In certain embodiments, the pharmaceutical composition comprises at least about 50 mg, at least about 100 mg, at least about 150 mg, at least about 200 mg, at least about 250 mg, at least about 300 mg, at least about 350 mg, at least about 400, at least about 450 mg, at least about 500 mg, at least about 550 mg, at least about 600 mg, at least about 650 mg, at least about 700 mg, at least about 750 mg, at least about 800 mg, at least about 850 mg, at least about 900 mg, at least about 950 mg, at least about 1000 mg, at least about 1050 mg, at least about 1100 mg, at least about 1150 mg, at least about 1200 mg, at least about 1250 mg, at least about 1300 mg, at least about 1350 mg, at least about 1400 mg, at least about 1450 mg, at least about 1500 mg, at least about 1550 mg, at least about 1600 mg, at least about 1650 mg, at least about 1700 mg, at least about 1750 mg or at least about 1800 mg N-acylethanolamine or a salt thereof. In certain embodiments, the pharmaceutical composition comprises about 50 mg, about 100 mg, about 150 mg, about 200 mg, about 250 mg, about 300 mg, about 350 mg, about 400, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg or about 1800 mg N-acylethanolamine or a salt thereof. Each possibility represents a separate embodiment of the present invention.

In certain embodiments, the N-acylethanolamine is selected from the group consisting of N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), salts thereof and any combination thereof. Each possibility represents a separate embodiment of the present invention. In certain embodiments, the N-acylethanolamine is PEA or a salt thereof. In certain embodiments, the N-acylethanolamine consists of PEA or a salt thereof. In certain embodiments, the N-acylethanolamine consists of PEA.

In certain embodiments, the mixture comprises THC or a salt thereof and PEA or a salt thereof. In certain embodiments, the mixture consists of THC or a salt thereof and PEA or a salt thereof. In certain embodiments, the mixture comprises THC and PEA. In certain embodiments, the mixture consists of THC and PEA. In certain embodiments, the mixture comprises about 1-9.5 mg, about 1.5-9 mg, about 2-8.5 mg, about 2.5-8 mg, about 3-7.5 mg, about 3.5-7 mg, about 4-6.5 mg, about 4.5-6 mg or about 5-5.5 mg THC or a salt thereof and about 250-1550 mg, about 300-1200 mg, about 350-950 mg, about 400-700 mg, about 450-600 mg or about 500-550 mg PEA or a salt thereof. In certain embodiments, the mixture comprises about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg or about 10 mg THC or a salt thereof and at least about 50 mg, at least about 100 mg, at least about 150 mg, at least about 200 mg, at least about 250 mg, at least about 300 mg, at least about 350 mg, at least about 400, at least about 450 mg, at least about 500 mg, at least about 550 mg, at least about 600 mg, at least about 650 mg, at least about 700 mg, at least about 750 mg, at least about 800 mg, at least about 850 mg, at least about 900 mg, at least about 950 mg, at least about 1000 mg, at least about 1050 mg, at least about 1100 mg, at least about 1150 mg, at least about 1200 mg, at least about 1250 mg, at least about 1300 mg, at least about 1350 mg, at least about 1400 mg, at least about 1450 mg, at least about 1500 mg, at least about 1550 mg, at least about 1600 mg, at least about 1650 mg, at least about 1700 mg, at least about 1750 mg or at least about 1800 mg PEA or a salt thereof. In certain embodiments, the mixture comprises about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg or 10 about mg THC or a salt thereof and about 50 mg, about 100 mg, about 150 mg, about 200 mg, about 250 mg, about 300 mg, about 350 mg, about 400, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg or about 1800 mg PEA or a salt thereof. In certain embodiments, the mixture comprises about 0.5-10 mg THC or a salt thereof and about 200-1800 mg PEA or a salt thereof. In certain embodiments, the mixture comprises about 2.5-10 mg THC or a salt thereof and about 250-1000 mg PEA or a salt thereof. In certain embodiments, the mixture comprises about 2.5 mg, about 5 mg, about 7.5 mg or about 10 mg THC or a salt thereof and about 250 mg, about 500 mg, about 750 mg or about 1000 mg PEA or a salt thereof. Each possibility represents a separate embodiment of the present invention.

In certain embodiments, the pharmaceutical composition is formulated for systemic administration. In certain embodiments, the pharmaceutical composition is formulated for oral, oral mucosal, nasal, sublingual, inhalational, topical, rectal, vaginal, parenteral, intravenous, intramuscular, or subcutaneous administration. In certain embodiments, the pharmaceutical composition is formulated for oral, oral mucosal, nasal, or sublingual administration. Each possibility represents a separate embodiment of the present invention. In certain embodiments, the pharmaceutical composition is formulated for oral administration. In certain embodiments, the pharmaceutical composition is formulated for oral mucosal administration. In certain embodiments, the pharmaceutical composition is formulated for nasal administration. In certain embodiments, the pharmaceutical composition is formulated for sublingual administration.

Techniques for formulation and administration of drugs are well known in the art, and may be found, e.g. in "Remington's Pharmaceutical Sciences," Mack Publishing Co., Easton, Pa. Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethyl-cellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

The term "oral administration" refers to any method of administration in which an active agent can be administered by swallowing, chewing, sucking, or drinking an oral dosage form. Examples of solid dosage forms include conventional tablets, multi-layer tablets, capsules, caplets, etc., which do not substantially release the drug in the mouth or in the oral cavity.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include stiff or soft, sealed capsules made of gelatin and a plasticizer, such as glycerol or sorbitol. The capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal and sublingual administration, the compositions may take the form of tablets or lozenges formulated in conventional manner or in adhesive carriers. Alternatively, the active ingredient may be in powder faun for constitution with a suitable vehicle, e.g., a sterile, pyrogen-free, water-based solution, before use.

Pharmaceutical compositions suitable for use in the context of the present invention include compositions wherein the active ingredients are contained in an amount effective to achieve the intended purpose. More specifically, a "therapeutically effective amount" means an amount of active ingredients effective to prevent, alleviate, or ameliorate symptoms or side effects of a disease or disorder, or prolong the survival of the subject being treated. Determination of a therapeutically effective amount is well within the capability of those skilled in the art, especially in light of the detailed disclosure provided herein. More specifically, a "therapeutically effective amount of a mixture" means an amount of at least two active ingredients, wherein each one of the active ingredients independently may not be in a therapeutically effective amount or wherein both of the active ingredients may not be in a therapeutically effective amount, the mixture is nevertheless effective to prevent, alleviate, or ameliorate symptoms or side effects of a disease or disorder, or prolong the survival of the subject being treated. The term "mixture" as used herein refers to a non-covalent combination of two molecules.

For any preparation used in the methods of the invention, the dosage or the therapeutically effective amount can be estimated initially from in vitro, in vivo and cell culture assays. For example, a dose can be formulated in animal models to achieve a desired concentration or titer. Such information can be used to more accurately determine useful doses in humans. The dosage of each compound of the claimed combinations depends on several factors, including: the administration method, the disease to be treated, the severity of the disease, whether the disease is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect dosage used. Continuous daily dosing may not be required; a therapeutic regimen may require cycles, during which time a drug is not administered, or therapy may be provided on an as-needed basis during periods of acute disease worsening. Dosage escalation may or may not be required; a therapeutic regimen may require reduction in medication dosage. Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human The dosage may vary depending upon the dosage form employed and the route of administration utilized. The exact formulation, route of administration, and dosage can be chosen by the individual physician in view of the patient's condition (See, e.g., Fingl, E. et al. (1975), "The Pharmacological Basis of Therapeutics," Ch. 1, p. 1). Depending on the severity and responsiveness of the condition to be treated, dosing can be of a single or a plurality of administrations, with course of treatment lasting from several days to several weeks, or until cure is effected or diminution of the disease state is achieved.

The present invention further provides, in another aspect, a dosage unit comprising or consisting of the pharmaceutical composition described above.

In certain embodiments, the dosage unit comprises the pharmaceutical composition described above. In certain embodiments, the dosage unit consisting of the pharmaceutical composition described above. In certain embodiments, the dosage unit is formulated as a gel, a powder or a spray. In certain embodiments, the dosage unit is formulated as a gel. In certain embodiments, the dosage unit is formulated as a powder. In certain embodiments, the dosage unit is formulated as a spray.

The present invention further provides, in another aspect, a pharmaceutical composition or a dosage unit as described above for use in a method for preventing or treating a condition amenable to prevention or treatment by at least one cannabinoid.

In certain embodiments, the pharmaceutical composition or a dosage unit as described above for use in a method for preventing or treating a condition amenable to prevention or treatment by at least one cannabinoid comprises the cannabinoid and the N-acylethanolamine in a molar ratio between about 1:15 to about 1:1800.

The present invention further provides, in another aspect, a pharmaceutical composition or a dosage unit as described above for use in a method for preventing or treating at least one symptom of a movement disorder.

In certain embodiments, the pharmaceutical composition or a dosage unit as described above for use in a method for preventing or treating at least one symptom of at least one symptom of a movement disorder comprises the cannabinoid and the N-acylethanolamine in a molar ratio between about 1:15 to about 1:1800.

In certain embodiments, the movement disorder is selected from Tic disorders, Tourette's syndrome, Parkinson's disease Hallevorden-Spatz disease, progressive supranuclear ophthalmoplegia, striatonigral deneneration, dystonia, spasmodic torticolis, blepharospasm, tremor, myoclonus, chorea, ballismus, hemiballismus, athetosis, dyskinesia, paroxysmal nocturnal limb movement, moving toes or fingers syndrome, restless leg syndrome, Stiff-person syndrome, abnormal head movements, cramp, spasm, and Fasciculation The present invention further provides, in another aspect, a pharmaceutical composition or a dosage unit as described above for use in a method for preventing or treating at least one symptom of Tourette syndrome.

The term "treating" as used herein, includes, but is not limited to, any one or more of the following: abrogating, ameliorating, inhibiting, attenuating, blocking, suppressing, reducing, delaying, halting, alleviating or preventing one or more symptoms or side effects of the diseases or conditions of the invention.

The term "acute" refers to a condition with a relatively short, severe course.

The term "chronic" as used herein means that the length of time of the diseases or conditions of the invention can be weeks, months, or possibly years. The intensity of the diseases or conditions can differentiate according to various conditions such as patient age, temperature, season, type of disease, etc.

In certain embodiments, the pharmaceutical composition or a dosage unit as described above for use in a method for preventing or treating at least one symptom of Tourette syndrome comprises the cannabinoid and the N-acylethanolamine in a molar ratio between about 1:15 to about 1:1800.

In certain embodiments, the Tourette syndrome is classified as mild Tourette syndrome. In certain embodiments, the Tourette syndrome is classified as moderate Tourette syndrome. In certain embodiments, the Tourette syndrome is classified as severe Tourette syndrome. In certain embodiments, the Tourette syndrome is classified as a moderate to severe Tourette syndrome. In certain embodiments, the symptom is tics. In certain embodiments, the tics are motor tics. In certain embodiments, the tics are phonic tics. In certain embodiments, the tics are verbal tics. In certain embodiments, the tics are vocal tics. In certain embodiments, the tics are simple motor tics. In certain embodiments, the tics are complex motor tics. In certain embodiments, the tics are simple phonic tics. In certain embodiments, the tics are complex phonic tics.

The present invention further provides, in another aspect, a pharmaceutical composition or a dosage unit as described above for use in a method for preventing or treating pain.

In certain embodiments, the pharmaceutical composition or a dosage unit as described above for use in a method for preventing or treating pain comprises the cannabinoid and the N-acylethanolamine in a molar ratio between about 1:0.2 to about 1:5.

Neuropathic pain is a localized sensation of unpleasant discomfort caused by damage or disease that affects the somatosensory system. The International Association for the Study of Pain (IASP) widely used definition of pain states: "Pain is an unpleasant sensory and emotional experience associated with actual or potential tissue damage, or described in terms of such damage". Therefore, the term "pain", as used herein, means an unpleasant sensory and emotional experience associated with actual or potential tissue damage, or described in terms of such damage. Neuropathic pain may be associated with abnormal sensations called dysesthesia, and pain from normally non-painful stimuli (allodynia). It may have continuous and/or episodic (paroxysmal) components. The latter resemble stabbings or electric shocks. Common qualities include burning or coldness, "pins and needles" sensations, numbness and itching. Nociceptive pain, by contrast, is more commonly described as aching. Central neuropathic pain is found in spinal cord injury, multiple sclerosis, and some strokes. Aside from diabetes and other metabolic conditions, the common causes of painful peripheral neuropathies are herpes zoster infection, HIV-related neuropathies, nutritional deficiencies, toxins, remote manifestations of malignancies, immune mediated disorders and physical trauma to a nerve trunk. Neuropathic pain is common in cancer as a direct result of cancer on peripheral nerves (e.g., compression by a tumor), or as a side effect of chemotherapy (chemotherapy-induced peripheral neuropathy), radiation injury or surgery.

In certain embodiments, the pain is an acute pain. In certain embodiments, the pain is chronic pain. In certain embodiments, the pain is neuropathic pain.

The present invention further provides, in another aspect, a pharmaceutical composition or a dosage unit as described above for use in a method for preventing or treating emesis.

In certain embodiments, the pharmaceutical composition or a dosage unit as described above for use in a method for preventing or treating emesis comprises the cannabinoid and the N-acylethanolamine in a molar ratio between about 1:15 to about 1:1800.

In certain embodiments, the emesis is caused by or is associated with a disease or condition selected from gastritis, ulcers, gastroparesis, poisoning, cancer, elevated intracranial pressure, motion sickness, seasickness, early stages of pregnancy, medication-induced vomiting, intense pain, emotional stress, gallbladder disease, infections, overeating, heart attack, concussion, brain injury, brain tumor, bulimia, and overexposure to ionizing radiation. Each possibility represents a separate embodiment of the invention.

In certain embodiments, the therapeutic potency of the pharmaceutical composition is increased compared to the same pharmaceutical composition without the N-acylethanolamine. In certain embodiments, the required therapeutic dosage of the cannabinoid in the pharmaceutical composition is decreased compared to the required therapeutic dosage of the cannabinoid in a similar pharmaceutical composition without the N-acylethanolamine. In certain embodiments, at least one of the side-effects of the cannabinoid in the pharmaceutical composition is reduced by the use of the pharmaceutical composition compared to the same side-effect while using a similar pharmaceutical composition without the N-acylethanolamine. In certain embodiments, the therapeutic window of the cannabinoid in the pharmaceutical composition is expended compared to the therapeutic window of the cannabinoid in a similar pharmaceutical composition without the N-acylethanolamine.

In certain embodiments, the N-acylethanolamine increases the therapeutic potency of the cannabinoid compared to the same pharmaceutical composition without the N-acylethanolamine. In certain embodiments, the N-acylethanolamine decreases the required therapeutic dosage of the cannabinoid compared to the same pharmaceutical composition without the N-acylethanolamine In certain embodiments, the N-acylethanolamine reduces at least one of the side-effects of the cannabinoid compared to the same pharmaceutical composition without the N-acylethanolamine. In certain embodiments, the N-acylethanolamine expends the therapeutic window of the cannabinoid compared to the same pharmaceutical composition without the N-acylethanolamine. In certain embodiments, the PEA or salt thereof increases the therapeutic potency of the THC or salt thereof compared to the same pharmaceutical composition without the PEA or salt thereof. In certain embodiments, the PEA or salt thereof decreases the required therapeutic dosage of the THC or salt thereof compared to the same pharmaceutical composition without the PEA or salt thereof. In certain embodiments, the PEA or salt thereof reduces at least one of the side-effects of the THC or salt thereof compared to the same pharmaceutical composition without the PEA or salt thereof. In certain embodiments, the PEA or salt thereof expends the therapeutic window of the THC or salt thereof compared to the same pharmaceutical composition without the PEA or salt thereof.

The phrase "N-acylethanolamine increases the therapeutic potency of the cannabinoid" as used herein refers to the significantly improved therapeutic effect of the cannabinoid when administered with an N-acylethanolamine, compared to the therapeutic effect of the cannabinoid when administered without the N-acylethanolamine The phrase "N-acylethanolamine decreases the required therapeutic dosage of the cannabinoid" as used herein refers to the significantly lower dosage required to achieve a certain therapeutic effect of the cannabinoid when administered with an N-acylethanolamine, compared to the N-acylethanolamine dosage required to achieve the same therapeutic effect when the cannabinoid is administered without the N-acylethanolamine.

The phrase "N-acylethanolamine reduces at least one of the side effects of the cannabinoid" as used herein refers to the significantly lower severity of at least one of the side effects of the cannabinoid when the cannabinoid is administered with an N-acylethanolamine, compared to the severity of the same side effect when the cannabinoid is administered without the N-acylethanolamine.

The phrase "N-acylethanolamine prolongs the therapeutic window of the cannabinoid" as used herein refers to the significantly longer period in which the cannabinoid has a therapeutic effect when administered with an N-acylethanolamine, compared to the period in which the cannabinoid has a therapeutic effect when administered without the N-acylethanolamine.

The present invention further provides, in another aspect, a pharmaceutical composition or a dosage unit as described above for use in a method for preventing or treating at least one side-effect associated with cannabinoid consumption.

In certain embodiments, the pharmaceutical composition or a dosage unit as described above for use in a method for preventing or treating at least one side-effect associated with cannabinoid consumption comprises the cannabinoid and the N-acylethanolamine in a molar ratio between about 1:0.2 to about 1:5.

Emesis (vomiting) is the involuntary, forceful expulsion of the contents of one's stomach through the mouth and sometimes the nose. Vomiting can be caused by a wide variety of conditions; it may present as a specific response to ailments like gastritis or poisoning, or as a non-specific sequela of disorders ranging from brain tumors and elevated intracranial pressure to overexposure to ionizing radiation. The feeling that one is about to vomit is called nausea, which often proceeds, but does not always lead to, vomiting. Antiemetics are sometimes necessary to suppress nausea and vomiting. In severe cases, where dehydration develops, intravenous fluid may be required.

Anorexia is the decreased sensation of appetite. While the term in non-scientific publications is often used interchangeably with anorexia nervosa, many possible causes exist for a decreased appetite, such as those listed above. Anorexia nervosa is an eating disorder characterized by a low weight, fear of gaining weight, a strong desire to be thin, and food restriction.

The primary effects of *Cannabis* are caused by the chemical compounds in the plant, including cannabinoids, such as tetrahydrocannabinol (THC). *Cannabis* has psychological and physiological effects on the human body. Cannabinoid consumption may lead to short and/or long-term effects. Short-term effects, generally ranging from 10 minutes to 8 hours, include, but are not limited to, psychoactive effects (known as a "high"), and somatic effects, such as increased heart rate, dry mouth, congestion of the conjunctival blood vessels (reddening of the eyes), reduction in intra-ocular pressure, muscle relaxation and a sensation of cold or hot hands and feet. Long-term effects include, but are not limited to, risk of irreversible cognitive impairment, anxiety, schizophrenia, and depression. *Cannabis* "use disorder" is defined as a medical diagnosis in the fifth revision of the Diagnostic and Statistical Manual of Mental Disorders (DSM-5).

In certain embodiments, the side-effect is increased appetite. In certain embodiments, the side-effect is body-weight gain. In certain embodiments, the side-effect is increased appetite and body-weight gain. In certain embodiments, the side-effect is confusion. In certain embodiments, the side-effect is disorientation. In certain embodiments, the side-effect is confusion and disorientation. In certain embodiments, the side-effect is anxiety.

The present invention further provides, in another aspect, a method for preventing or treating a condition amenable to prevention or treatment by at least one cannabinoid in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof.

In certain embodiments, the condition is an acute or a chronic neuropathic pain. In certain embodiments, the pain is caused by or is associated with a disease or condition selected from diabetes, an adverse metabolic condition, herpes zoster infection, an HIV-related neuropathy, a nutritional deficiency, a toxin, a malignancy, an immune mediated disorder, a physical trauma, a chemotherapy-induced peripheral neuropathy, alcoholism, multiple sclerosis, radiation injury or surgery. Each possibility represents a separate embodiment of the invention.

In certain embodiments, the condition is emesis. In certain embodiments, the emesis is caused by or is associated with a disease or condition selected from gastritis, ulcers, gastroparesis, poisoning, cancer, elevated intracranial pressure, motion sickness, seasickness, early stages of pregnancy, medication-induced vomiting, intense pain, emotional stress, gallbladder disease, infections, overeating, heart attack, concussion, brain injury, brain tumor, bulimia, and overexposure to ionizing radiation. Each possibility represents a separate embodiment of the invention.

In certain embodiments, the condition is anorexia. In certain embodiments, the anorexia is caused by or is associated with a disease or condition selected from acquired immune deficiency syndrome (AIDS), acute radiation syndrome, acute viral hepatitis, addison's disease, atypical pneumonia, (mycoplasma), anorexia nervosa, anxiety disorder, appendicitis, cancer, chronic pain, chronic kidney disease, congestive heart failure, congestion of the liver with venous blood, Crohn's disease, dehydration, dementia, drug addiction, depression, hypervitaminosis D, a metabolic disorder, an urea cycle disorder, sickness behavior, superior mesenteric artery syndrome, tuberculosis, thalassemia, ulcerative colitis, and zinc deficiency. Each possibility represents a separate embodiment of the invention.

In certain embodiments, the condition is a side effect associated with cannabinoid consumption. In certain embodiments, the side effect is caused by or is associated with a disease or condition selected from acute impaired cognitive function, and hypertriglyceridemia. In certain embodiments, the acute impaired cognitive function is selected from the group consisting of an impaired ability to plan, of an impaired ability to organize, of an impaired ability to solve problems, of an impaired ability to make decisions, and of an impaired ability to control impulses. Each possibility represents a separate embodiment of the invention.

The present invention further provides, in another aspect, a method for preventing or treating at least one symptom of Tourette syndrome in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, thereby preventing or treating the at least one symptom of Tourette syndrome.

The present invention further provides, in another aspect, a method for preventing or treating pain m a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, thereby preventing or treating pain.

The present invention further provides, in another aspect, a method for preventing or treating emesis in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, thereby preventing or treating emesis.

The present invention further provides, in another aspect, a method for preventing or treating at least one side-effect associated with cannabinoid consumption in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, thereby preventing or treating the at least one side-effect.

The present invention further provides, in another aspect, a method for preventing or treating a condition amenable to prevention or treatment by at least one cannabinoid in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating the condition.

The present invention further provides, in another aspect, a method for preventing or treating at least one symptom of Tourette syndrome in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating the at least one symptom of Tourette syndrome.

The present invention further provides, in another aspect, a method for preventing or treating pain in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating pain.

The present invention further provides, in another aspect, a method for preventing or treating emesis in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating emesis.

The present invention further provides, in another aspect, a method for preventing or treating at least one side-effect associated with cannabinoid consumption in a human subject in need thereof, the method comprising the step of administering to the subject a therapeutically-effective amount of a combination of a pharmaceutical composition comprising at least one cannabinoid or a salt thereof and a pharmaceutical composition comprising at least one N-acylethanolamine or a salt thereof, wherein the molar ratio between the administered cannabinoid and N-acylethanolamine is between about 1:0.2 to about 1:2000, thereby preventing or treating the at least one side-effect.

In certain embodiments of the methods described above, the cannabinoid and the N-acylethanolamine are comprised in the same pharmaceutical composition. In certain embodiments of the methods described above, the cannabinoid and the N-acylethanolamine are comprised in different pharmaceutical compositions.

In certain embodiments of the methods described above, the administration of the cannabinoid and the N-acylethanolamine is repeated. In certain embodiments of the methods described above, the administration of the cannabinoid and the N-acylethanolamine is repeated three times a day. In certain embodiments of the methods described above, the administration of the cannabinoid and the N-acylethanolamine is repeated twice a day. In certain embodiments of the methods described above, the administration of the cannabinoid and the N-acylethanolamine is repeated once a day. In certain embodiments of the methods described above, the administration of the cannabinoid and the N-acylethanolamine is repeated once every two days. In certain embodiments of the methods described above, the administration of the cannabinoid and the N-acylethanolamine is repeated once every three days.

In certain embodiments of the methods described above, the administration of the cannabinoid and the N-acylethanolamine is repeated until achieving a beneficial change in the condition of the subject according to the Yale Global Tic Severity Scale (YGTSS) compared to his condition prior to treatment. In certain embodiments of the methods described above, the administration of the cannabinoid and the N-acylethanolamine is repeated until achieving a beneficial change in the condition of the subject according to at least one scale selected from the group consisting of (i) the Clinician Global Impression scale (CGIS), (ii) the Gilles de la Tourette Syndrome-Quality Of Life scale (GTS-QOL) (iii) the Tourette Syndrome Symptom List (TSSL) (iv) the Yale-Brown Obsessive Compulsive Scale (Y-BOCS) (v) the ADHD Rating Scale-IV (ADHD-RS) and (vi) the Hamilton Anxiety Rating Scale (HAM-A), compared to his condition prior to treatment. Each possibility represents a separate embodiment of the present invention.

The term "about" as used herein in relation to a value, a plurality of values or a range of values defined by a lowest and highest values means a value which is 10% lower and/or higher than the corresponding value, plurality of values or range of values. For example, the phrase "about 1" means "0.9 to 1.1", the phrase "about 1 or 2" means "0.9 to 1.1 or 1.8 to 2.2", and the phrase "about 1 to about 2" means "0.9 to 2.2".

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

The following examples are presented in order to more fully illustrate some embodiments of the invention. They should, in no way be construed, however, as limiting the broad scope of the invention.

EXAMPLES

Materials and Methods

THC formulation for 50 and 12.5 mg/kg dose levels—THC arrived at a 16.7% (Dronabinol) concentration in sesame oil. THC was diluted in a 1:1:18 ratio of ethanol:cremophor:saline mixture. In order to achieve a 5 mghnl concentration at 100% dose, 200 µl were mixed with 325 µl ethanol, with 325 µl cremophor and diluted in 5850 µl saline. The same mixture was diluted ×4 with 1.3 ml ethanol, 1.3 ml cremophor and 23.4 ml saline in order to achieve 1.25 mg/ml concentration. The formulations were prepared twice, once for the open field test and again for the tail pinch test.

PEA formulation for 25 mg/kg dose level—PEA was prepared at a 5 mg/ml concentration by dissolving 30 mg PEA in 6 ml of ethanol:cremophor:saline mixture at a 1:1:18 ratio. To prepare 2.5 mg/ml PEA, 4 ml from the previous mixture were diluted with 4 ml of ethanol:cremophor:saline mixture at a 1:1:18 ratio. The formulations were prepared twice, once for the open field test and again for the tail pinch test.

Animals—Mice, strain ICR, male, 8 weeks of age at study initiation. The average animal body weight at study initiation was in the range of 31.97±1.61 g. The minimum and maximum weight in each group did not exceed ±20% of group mean weight. Animals were randomly allocated to individual cages on the day of reception. Animals were acclimated for seven to nine days.

TABLE 1

Group allocation

| Group | Test item (mg/kg) | N | Dose Volume (ml/kg) |
|---|---|---|---|
| 1M | Vehicle | 6 | 10 |
| 2M | THC (50) | 5 | |
| 3M | THC (12.5) | 6 | |
| 4M | PEA (25) + THC (50) | 6 | |
| 5M | PEA (25) + THC (12.5) | 6 | |

Test item was administered TP at a dose volume of 10 ml/kg according to the doses in Table 1. Dosing was performed 15 minutes before each of the behavioral tests.

TABLE 2

Equivalent Murine/Human dosages

| Group | Test item | Murine dose | Human dose | Drug molar ratio * |
|---|---|---|---|---|
| 2M | THC | 50 mg/kg | | — |
| 3M | THC | 12.5 mg/kg | | — |
| 4M | THC | 50 mg/kg | | 2 |
| | PEA | 25 mg/kg | | 1 |
| 5M | THC | 12.5 mg/kg | | 1 |
| | PEA | 25 mg/kg | | 2 |
| THX-TP-05 | THC | | 5 mg | 1 |
| | PEA | | 518 mg | 100 |
| THX-TP-10 | THC | | 10 mg | 1 |
| | PEA | | 518 mg | 50 |

* The M.W of THC is 314.469 g/mol, and the M.W of PEA is 299.50 g/mol.

Open Field (OF) tests were performed as follows—Fifteen minutes after test item/vehicle administration, mice were placed at the center of an open field box (43×43×40 cm) between 9 AM and 5 PM. On each side of the open field box, two frames placed at 2 and 5 cm height with 16 photocell beams per side ensure movement detection. The computer defined grid lines that divided the open field into two compartments: margin and center. Several variables were recorded during a 15 minute session of spontaneous activity including: time spent moving, traveled distance, time spent and number of visits to the central compartment.

Tail pinch tests were performed as follows, according to the modified Haffner's method (as depicted in Takagi et al., Jpn. J. Pharmacol., 1966, 16, Pages 287-294)—Mice were pretested by pinching their tail base with an artery clip (1.5 mm width, constant force), and only the mice that show a nociceptive response such as biting the clip or vocalizing within 2 sec were used for experiments. When the mice did not show the above-mentioned behaviors up to 6 sec after pinching, the antinociceptive effect was regarded as positive. To prevent tissue damage, the pressure stimuli was not applied for more than 10 sec. After drug treatments, the nociceptive response in the tail-pinch test was measured at varying intervals.

Statistical analysis—Numerical results were given as means±standard error of the mean. The results were subjected either to a T-test or to two-way ANOVA, followed by Bonferroni post-hoc contrast analysis between the groups where applicable. A probability of less than 5% ($p<0.05$) was regarded as significant.

Example 1

Body Weight Gain

Body weight (BW) gain was observed in all groups throughout the study. BW gain was significantly reduced ($p<0.01$) in group 4M and increased ($p<0.05$) in group 3M compared to group 1M. Group averages as BW (±SEM) percentage change from arrival throughout the study are presented in FIG. 1.

Figure 1B:
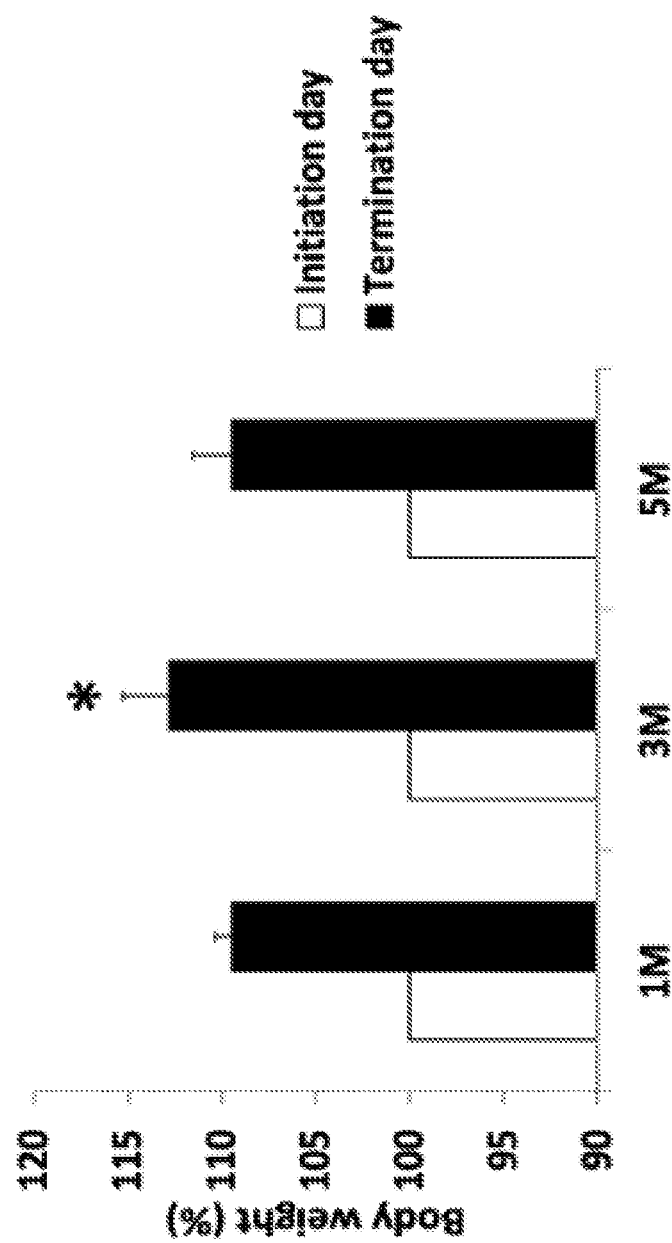

The data presented in FIGS. 1A and 1B demonstrates the characteristic weight gain commonly associated with cannabinoid uptake (2M and 3M vs. 1M, respectively), and the prevention or reduction of this adverse side-effect upon co-administration of N-acylethanolamines (4M and 3M vs. 5M respectively).

Example 2

Animal Velocity

Figure 2:
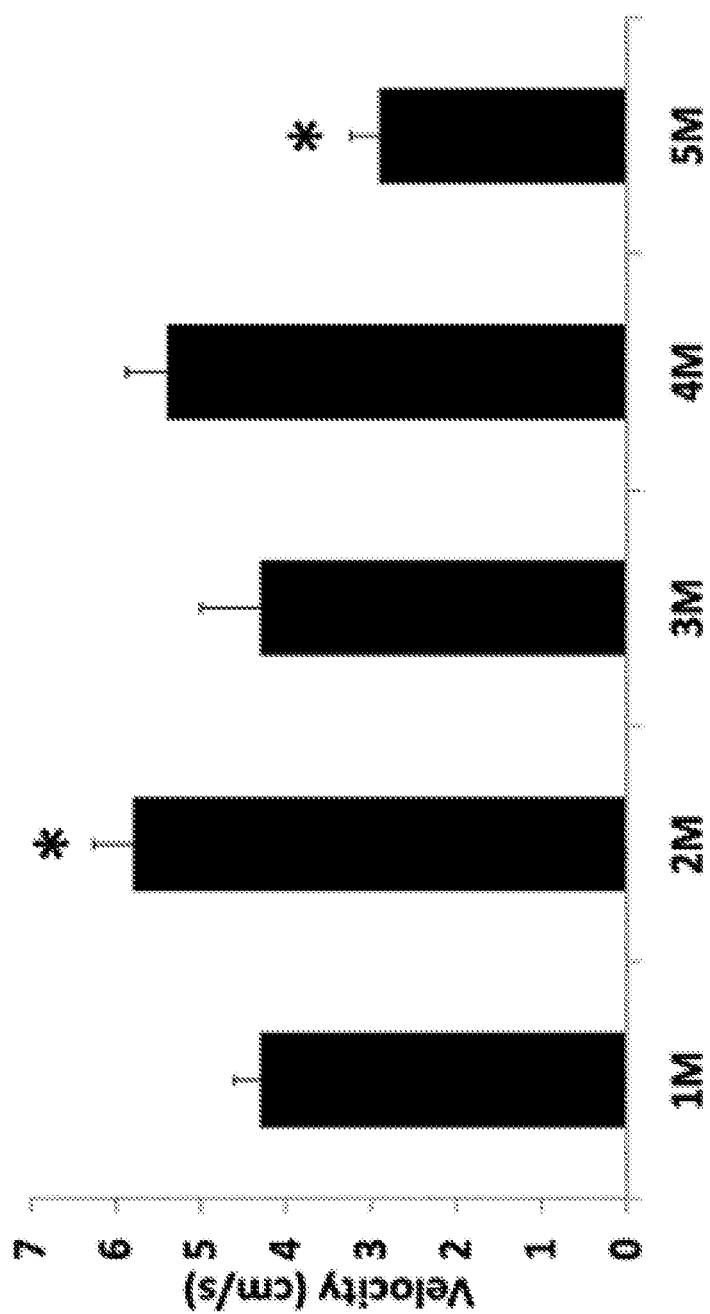
FIG. 2 is a bar graph illustrating different group averages of animal velocity during evaluation in an open field test.

Average animal velocity, associated in mice with uncontrolled movement was calculated by dividing the total distance traveled (cm) by each animal by the total moving time (sec) during a 15 minute session in an open field test. THC at 50 mg/kg significantly increased the velocity compared to control (2M vs. 1M) while THC at 12.5 mg/kg (3M) had no effect. PEA in combination with THC at 50 mg/kg (4M) had only moderately affected velocity (4M), while PEA in combination with THC at 12.5 mg/kg (SM) significantly reduced the velocity. Of particular interest, only group 2M, but not group 4M, demonstrated a significant increased level of uncontrolled movement. Of another particular interest, only group 5M, but not group 3M, demonstrated a significant reduced level of uncontrolled movement. Together, the data presented in FIG. 2 demonstrates that co-administration of N-acylethanolamines, in addition to cannabinoid uptake, is able to significantly prevent or reduce uncontrolled movement in mice. This ability is equivalent to preventing or minimizing adverse side-effects in human commonly associated with cannabinoid uptake, such as confusion and/or disorientation (Metrik J. et al., J. Cogn. Psychother., 2011, pages 1-18).

Example 3

Time Spent in the Center of an Arena

Figure 3:
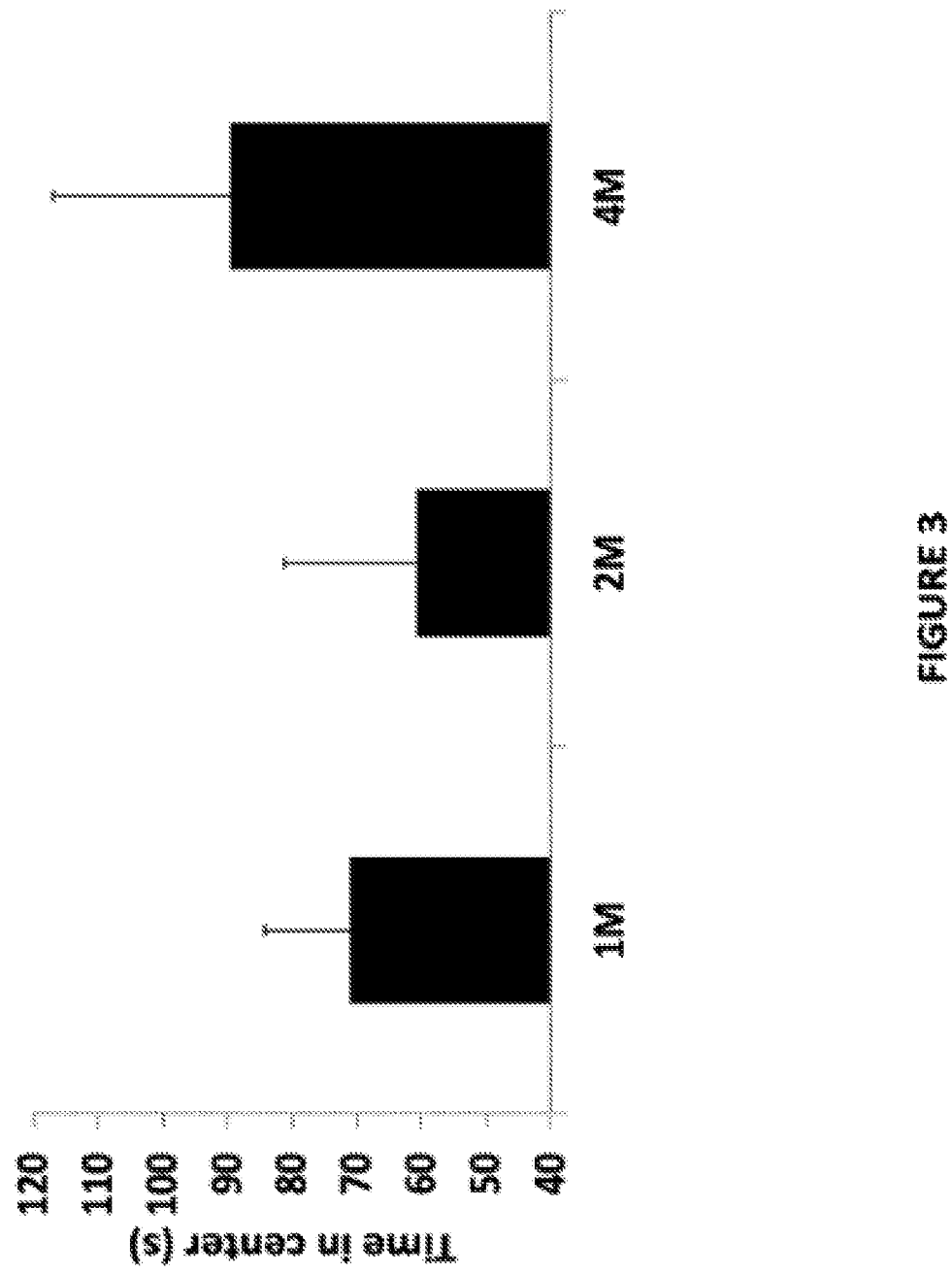
FIG. 3 is a bar graph illustrating different group averages of total time spent in the center of an arena during evaluation in an open field test.

Total time spent in the center of an arena, which is a measure of anxiety, was evaluated during a 15 minute session in the open field test. THC at 50 mg/kg (2M) had decreased the time spent in the center, while PEA combined with THC at 50 mg/kg (4M) had increased the time spent in the center. The data presented in FIG. 3 demonstrates that co-administration of N-acylethanolamines, in addition to cannabinoid uptake, is able to prevent or reduce anxiety, another adverse side-effect in human commonly associated with cannabinoid uptake.

Example 4

Tail Pinch Test

Figure 4A:
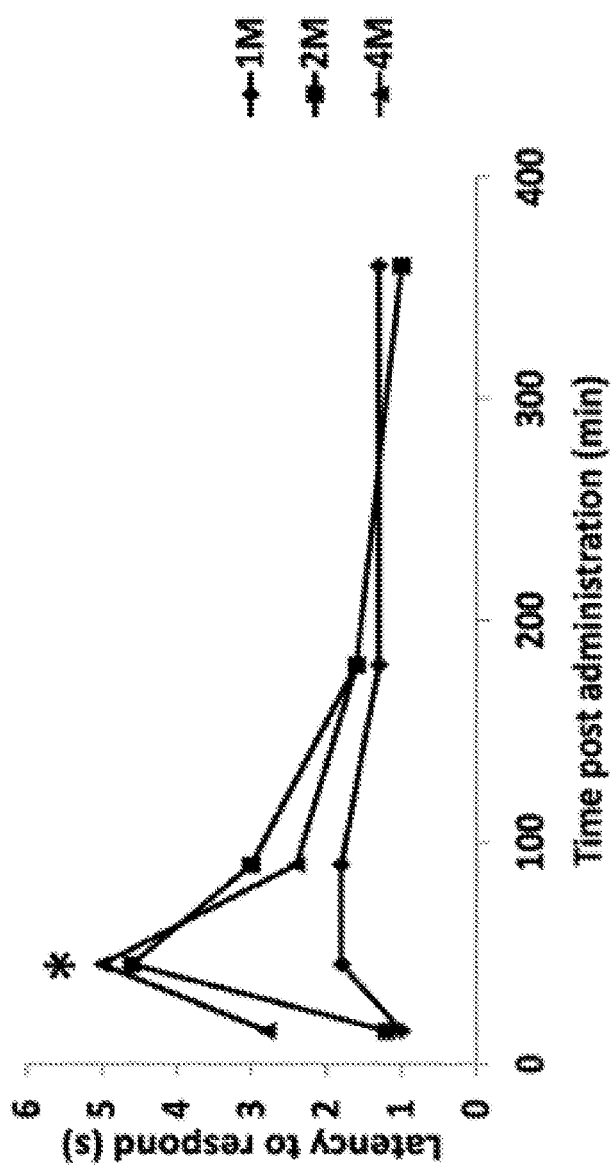
FIGS. 4A and 4B are bar graphs illustrating different group averages of latency to respond in a tail pinch test.

The tail pinch test was performed 15 minutes after the administration of the indicated test item. Pressure was applied to the base of the tail for no more than 10 seconds. The latency to respond in the high dose THC treated group (2M) was higher compared to the control as can be seen in FIG. 4A. Addition of PEA to the high dose THC further significantly enhanced the latency time of the high dose THC (4M). Of particular interest, at 15' post administration only group 4M exhibited an analgesic effect, which attests to the potential of the combination of N-acylethanolamines and cannabinoids in achieving an almost immediate analgesic effect. As depicted in FIG. 4A, the combination of N-acylethanolamines and cannabinoids is particularly potent 45' post administration. Thus, the combination of N-acylethanolamines and cannabinoids is both fast-acting and highly-potent in preventing or minimizing pain.

Figure 4B:
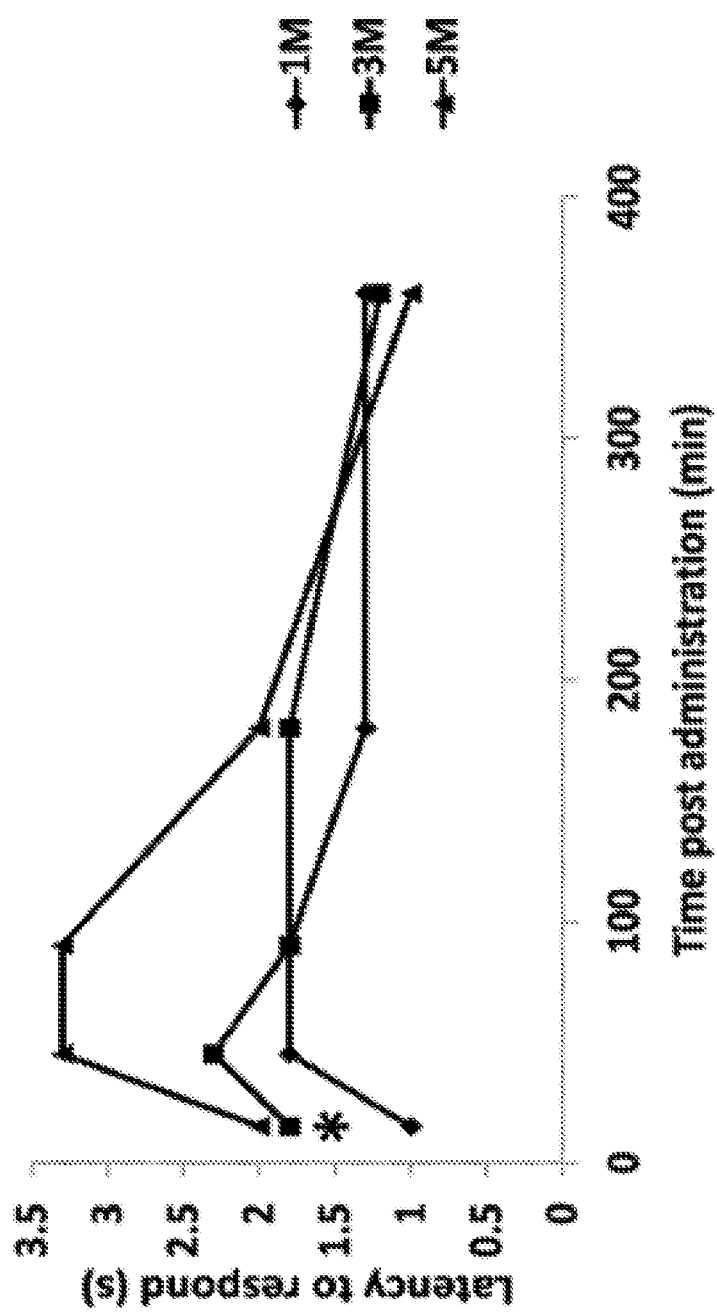

The latency to respond in the low dose THC treated group (3M) was higher compared to the control as can be seen in FIG. 4B. Addition of PEA to the low dose THC further significantly enhanced the latency time of the low dose THC (5M). Of particular interest, at 15' post administration both groups 3M and 5M exhibited an analgesic effect. As depicted in FIG. 4B, the combination of N-acylethanolamines and cannabinoids is particularly potent 45' and 90' post administration. Thus, the combination of N-acylethanolamines and cannabinoids is fast-acting, highly-potent and long-lasting in preventing or minimizing pain. The data presented in FIG. 4B is particularly surprising since the minimal effective dose of THC as an analgesic is widely considered to be 20 mg/kg (Buxbaum D M., Psychopharmacologia, 1972, Vol. 25(3), pages 275-280). Therefore, groups 3M and 5M, both relating to the administration of 12.5 mg/kg THC, which is considered a sub-therapeutic dose, were not expected to provide any measurable analgesic effect.

Example 5

Phase IIa, Randomized, Double-Blind, Parallel-Group, Placebo Controlled Study

Study groups—THX-TP-2.5-10 (A capsule of 2.5-10 mg Dronabinol® and 2 capsules of 259 mg PEA). For example, THX-TP-05 (A capsule of 5 mg Dronabinol® and 2 capsules of 259 mg PEA) and THX-TP-10 (A capsule of 10 mg Dronabinol® and 2 capsules of 259 mg PEA). Control group—Placebo.

Overall Study Design: A multicenter, randomized, double-blind, parallel-group, placebo-controlled study designed to evaluate the tolerability, safety and efficacy of once daily oral THX-TS in treating adults with moderate to severe Tourette syndrome according to DSM-V criteria. The dosage is titrated up to the target dosage and the same dosing schedule is used to reduce medication at the end of the treatment period. The study is comprised of two main phases: a treatment phase and a follow-up phase. Eligible consenting subjects are randomized in a double-blind fashion in a 1:1:1 ratio to receive study treatment (TRX-TS-05 or THX-TS-10) or placebo (Control).

Treatment Phase (6-10 weeks): Subjects receive once a day treatment for 6-10 weeks. Visits during the treatment phase commence on Day 0 with a total of 5 visits. The final double blind treatment visit occurs on TP5, about 6-10 weeks after baseline visit. Follow-Up Phase (4 weeks): Subjects after completing the treatment phase continue into the Follow-Up phase, returning for study visits after study medication is gradually stopped. The first follow up visit (FU1) occurs within 2 days after the study medication is gradually stopped by down titration followed by a termination visit up to 4 weeks after study medication complete withdrawal.

Baseline visit: Assessments at Baseline include: Vital signs (temperature, pulse, blood pressure); Laboratory testing (Blood and urine tests of dronabinol and its metabolites to exclude additional *Cannabis* use and to control compliance); Assessment of physiological symptoms (motor and vocal tics); Assessment of cognitive functions; Adverse events (AEs) and Concomitant medications; Subjects who meet all eligibility criteria, as per data gathered from Screening and Baseline visits, are randomized. All patients who fail to meet eligibility criteria at Baseline are considered screen failures and are exited the study without further evaluation.

Randomization: After subject is reviewed by the Principal Investigator to confirm the patient's eligibility for the trial the patient is randomized. Randomization is performed by the Principal Investigator. Both the Principal Investigator and the subject remain blinded to the study treatment.

Treatment Phase: The initial treatment is administered within 1 day after Randomization. Patients receive study treatment throughout the Treatment Phase. During Treatment Phase, several assessments are performed, including but not limited to Physical examination; Vital signs (temperature, pulse, blood pressure); Laboratory tests of serum chemistry, liver and renal function tests, hematology, serum pregnancy test; Laboratory testing (Blood and urine tests of dronabinol and its metabolites to exclude additional *Cannabis* use and to control compliance); Assessment of physiological symptoms (motor and vocal tics); Assessment of cognitive functions; Adverse events (AEs) and concomitant medications;

End of Treatment Phase: Once the 6-10 weeks of treatment are completed and the study medication withdrawal, the subject completes participation in this phase and moves into the follow up phase. At the last visit, (TP5), the subject undergoes all TP assessments, as described above.

Follow Up phase: All subjects who complete the Treatment Phase, complete the TP5 assessments and enter follow up phase. In the Follow Up phase, subjects return for 2 follow up assessments, one within 2 days of drugs withdrawal. At these visits, the following assessments are performed: Vital signs (heart rate, temperature, blood pressure); Adverse event inventory and update of concomitant medications and therapies. The primary objective of the study is to evaluate the clinical benefit of once-daily application of THX-TS in reducing total tic severity in adults with Tourette's Syndrome compared to placebo at up to 10 weeks following baseline visit. Additional objectives are to demonstrate safety and tolerability of THX-TS (study drug) compared to placebo (Control). Patients are randomized to treatment with either study combination drug or placebo based on 1:1:1 assignment ratio.

Inclusion Criteria: To be eligible for the study, subjects must fulfill all of the following criteria at Screening and Baseline, as applicable: (1) Males or females between 6 and 65 years of age (inclusive) with a diagnostic and Statistical Manual of Mental Disorders, Fifth Edition (DSM-V) diagnosis of Tourette syndrome or chronic motor tic disorder; (2) Subjects must sign an informed consent that complies with International Conference on Harmonization (ICH) guidelines and applicable local regulatory requirements prior to undergoing any study-related procedures; (3) Have at least moderate tic severity; or (4) Yale Global Tic Severity Scale Score (YGTSS) ≥20 with TS diagnosis or ≥14 for a Chronic Tic disorder; (5) Subjects with comorbid conditions: a mild degree of Oppositional defiant disorder (ODD) or Attention Deficit Hyperactivity Disorder (ADHD) and mild to moderate degree of Obsessive Compulsive Disorder (OCD); (6) Patient is in good general health, as indicated by medical and major psychiatric disorders history and physical examination. (7) Subjects must agree to avoid alcohol and substance abuse (e.g. amphetamines, barbiturates, benzodiazepine, phencyclidine, cocaine, or opiates); (8) Women of childbearing potential must have a negative serum pregnancy test and will use at least one reliable form of birth control (e.g. oral contraceptive for at least 3 months prior to screening or an intrauterine device or a combination of condom and spermicide) throughout the study; (9) Subjects must agree to comply with drug application regimen;

Exclusion Criteria: Patients meeting any of the following criteria will be excluded from the study at Screening and Baseline, as applicable: (1) Subjects with an active, clinically significant unstable medical condition within 1 month prior to screening; (2) Patient with a progressive or degenerative neurological disorder and major psychiatrics disorder that preclude the patients from participating in the study other than TS, ADHD, ODD, OCD, or a structural disorder of the brain; (3) Subjects with a known allergy, hypersensitivity, or intolerance to *Cannabis*, cannabinoids, fish oil, sesame oil, canola oil or any of the drugs compounds; (4) Subjects that have initiated Comprehensive Behavioral Intervention for Tics (CBIT) during the screening period or at baseline or plan to initiate CBIT during the study; (5) Patient is currently being treated with deep brain stimulation for control of tics; (6) Subjects that have received an investigational drug or device trial within 30 days before screening or plan to use an investigational drug (other than THX-TS-05 and THX-TS-10) during the study; (7) Any condition, which in the opinion of the Investigator, would interfere with the evaluation of the study product or poses a health risk to the subject.

Dose, Route & Dosage Form: All dosages of THX-TS (such as THX-TP-05, THX-TP-10) or placebo should be orally administered at least once a day, for example twice a day or trice a day, until study completion; The dosage will be titrated to a target dosage of dronabinol. Starting at 2.5 mg per day, the dose will be increased by increments of 2.5 mg per day until the desired dose is achieved; PEA dosage is constant throughout the treatment phase (518 mg/day); If a subject could not tolerate the maximum dose, an adjustment could be made by decreasing study medication, until a tolerated dose is achieved; Subjects assigned to the placebo group will receive identical placebo throughout the study in a similar fashion; Patients will be instructed to take the medication once a day in the morning together with breakfast.

Outcome Measures

Primary Efficacy Endpoint: The primary efficacy endpoint is the change from baseline to end of treatment phase in the Yale Global Tic Severity Scale (YGTSS).

Secondary Efficacy Endpoints: The secondary efficacy endpoints are the following: Change from baseline to end of treatment phase in Clinician Global Impression Scale (CGIS); Change from baseline to end of treatment phase in Gilles de la Tourette syndrome-quality of life scale (GTS-QOL); Change from baseline to end of treatment phase in Tourette Syndrome Symptom List (TSSL); Change from baseline to end of treatment phase in Yale-Brown Obsessive Compulsive scale (Y-BOCS); Change from baseline to end of treatment phase in ADHD Rating Scale-IV (ADHD-RS); Change from baseline to end of treatment phase in Hamilton Anxiety Rating Scale (HAM-A); Proportion of patients with a negative outcome related to Tourette syndrome, defined by any of the following events during the treatment phase: worsening of tic severity and/or in comorbid conditions, early discontinuation from study due inadequate effect or adverse events.

Tolerability Endpoints: The tolerability measures are as follows: Proportion of patients who discontinued early from the study; Proportion of patients who discontinued study treatment early due to adverse experiences; Proportion of patients who withdrew from the study; Time to early study discontinuation; Time to early study treatment discontinuation due to adverse events; and Time to withdrawal from the study.

Safety Endpoints: The safety endpoints are the following: Frequency and type of AEs; Intensity of AEs; Frequency and type of related AEs; Frequency and type of SAEs; Change From Baseline in Suicidal Ideation Intensity Total Score Based on Columbia-Suicide Severity Rating Scale (C-SSRS); Assessment of Cognitive Function: German Version of Auditory Verbal Learning Test (VLMT); Benton Visual Retention Test (BVRT); Divided Attention (TAP); Multiple Choice Vocabulary Test (NWT-B).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for preventing or treating pain in a human subject in need thereof, comprising
administering to the subject a pharmaceutical composition in a therapeutically-effective amount to prevent or treat the pain,
wherein the composition comprises at least one phyto-cannabinoid or a salt thereof, and at least one N-acylethanolamine or a salt thereof,
wherein the at least one phyto-cannabinoid or salt thereof and the at least one N-acylethanolamine or salt thereof are present in the composition in a molar ratio of about 1:0.2 to about 1:2000, and
wherein the at least one phyto-cannabinoid is tetrahydrocannabinol (THC) or a salt thereof.

2. The method of claim 1, wherein the molar ratio between the at least one phyto-cannabinoid or salt thereof, and the at least one N-acylethanolamine or salt thereof is between about 1:0.2 to about 1:5.

3. The method of claim 1, wherein the molar ratio between the at least one phyto-cannabinoid or salt thereof, and the at least one N-acylethanolamine or salt thereof is between about 1:0.5 to about 1:2.

4. The method of claim 1, wherein the molar ratio between the at least one phyto-cannabinoid or salt thereof, and the at least one N-acylethanolamine or salt thereof is between about 1:15 to about 1:1800.

5. The method of claim 1, wherein the molar ratio between the at least one phyto-cannabinoid or salt thereof, and the at least one N-acylethanolamine or salt thereof is between about 1:25 to about 1:450.

6. The method of claim 1, wherein the molar ratio between the at least one phyto-cannabinoid or salt thereof, and the at least one N-acylethanolamine or salt thereof is between about 1:50 to about 1:100.

7. The method of claim 1, wherein the pharmaceutical composition comprises about 200-1800 mg of N-acylethanolamine or salt thereof.

8. The method of claim 7, wherein the pharmaceutical composition comprises about 250 mg, about 500 mg, about 750 mg, about 1000 mg or about 1500 mg of N-acylethanolamine or salt thereof.

9. The method of claim 1, wherein the at least one N-acylethanolamine is N-palmitoylethanolamine (PEA), Me-palmitoylethanolamide (Me-PEA), palmitoylcyclohexamide, palmitoylbutylamide, palmitoylisopropylamide, oleoylethanolamine (OEA), palmitoylisopropylamide (PIA), a salt thereof, or any combination thereof.

10. The method of claim 9, wherein the at least one N-acylethanolamine is PEA or a salt thereof.

11. The method of claim 1, wherein the pharmaceutical composition comprises THC or a salt thereof, and PEA or a salt thereof.

12. The method of claim 1, wherein the pharmaceutical composition comprises about 0.5-10 mg of THC or a salt thereof, and about 200-1800 mg of PEA or a salt thereof.

13. The method of claim 1, wherein the pharmaceutical composition comprises about 2.5-10 mg of THC or a salt thereof and about 250-1000 mg of PEA or a salt thereof.

14. The method of claim 1, wherein the pharmaceutical composition comprises about 2.5 mg, about 5 mg, about 7.5 mg or about 10 mg of THC or a salt thereof, and about 250 mg, about 500 mg, about 750 mg or about 1000 mg of PEA or a salt thereof.

15. The method of claim 1, wherein the pharmaceutical composition is formulated for oral, oral mucosal, nasal, sublingual, inhalational, topical, rectal, vaginal, parenteral, intravenous, intramuscular, or subcutaneous administration.

16. The method of claim 1, wherein the administration of the at least one phyto-cannabinoid and the N-acylethanolamine is repeated.

17. The method of claim 1, wherein the pain is an acute pain, chronic pain, or neuropathic pain.

* * * * *